US006570063B1

(12) United States Patent
Butler et al.

(10) Patent No.: US 6,570,063 B1
(45) Date of Patent: May 27, 2003

(54) MAGNESIUM CHELATASE

(75) Inventors: Karlene H. Butler, Newark, DE (US); Omolayo O. Famodu, Newark, DE (US); Carl A. Maxwell, Elkton, MD (US)

(73) Assignee: E.I. duPont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/585,173

(22) Filed: Jun. 1, 2000

Related U.S. Application Data
(60) Provisional application No. 60/137,461, filed on Jun. 4, 1999.

(51) Int. Cl.$^7$ .......................... A01H 3/00; C07H 21/04; C07K 14/415; C12N 5/14; C12N 9/00

(52) U.S. Cl. .......................... 800/278; 435/6; 435/69.1; 435/183; 435/410; 435/419; 435/252.3; 435/320.1; 530/350; 530/370; 536/23.1; 536/23.2; 536/23.6; 536/24.1; 536/24.3; 800/295

(58) Field of Search .......................... 435/6, 69.1, 183, 435/410, 419, 252.3, 320.1; 530/350, 370; 536/23.1, 23.2, 23.6, 24.1, 24.3; 800/278, 295

(56) References Cited

FOREIGN PATENT DOCUMENTS

| DE | 19717656 | * 10/1998 |
|---|---|---|
| EP | 0 953 646 A2 | 11/1999 |
| WO | 98/49330 | 11/1998 |
| WO | 99/22011 | 5/1999 |

OTHER PUBLICATIONS

Database EMBL Accession No. AW781791, May 14, 2000, Shoemaker, R. et al., Public Soybean EST Project, XP002149706.
Database Biosis, Biosciences Information Service, Mar. 1998, Nakayama Masato et al., Cloning and Expression of the Soybean ch1H Gene Encoding a Subunit of Mg–chelatase and Localizatin of the Mg2+Concentration–dependent ch1H Protein within the Chloroplast, Database Accession No. PREV199800211900, XP002149707.
Masato Nakayama et al., Plant Cell Phys., vol. 39(3):275–284, 1998, Cloning and Expression of the Soybean ch1H Gene Encoding a Subunit of Mg–chelatase and Localization of the Mg2+Concentration–dependent ch1H Protein within the Chloroplast.
Database Biosis, Biosciences Information Service, 1996, Falbel Tanya G. et al., Partial Blocks in the Early Steps of the Chlorophyll Synthesis Pathway: A Common Feature of Chlorophyll Synthesis Pathway: A common feature of chlorophyll beta–deficient mutants, Database Accession No. PREV199699108594, XP002149708.

Tanya G. Falbel et al., Physiologia Plantarum, vol. 97:311–320, 1996, Partial blocks in the early steps of the chlorophyll synthesis pathway: A common feature of chlorophyll–beta–deficient mutants.
Jutta Papenbrock et al., The Plant Journal, vol. 12(5):981–990, 1997, Mg–chelatase of Tobacco: Identification of a Chl D cDNA Sequence Encoding a Third Subunit, Analysis of the Interaction of the Three Subunits with the Yeast Two–hybrid System, and Reconstitution of the Enzyme Activity by Co–expression of Recombinant CHL D, CHL H and CHL L.
Database EMBL Accession No. Y10022, Jul. 1, 1997, Papenbrock, J. et al., N. Tabacum mRNA for CHLD Magnesium Chelatase Subunit, XP002076481.
Ribo Guo et al., Plant Phys., vol. 116:605–615, 1998, Mageisum–Chelatase from Developing Pea Leaves.
Database EMBL Accession No. AF014399, Aug. 23, 1997, Luo, M. et al., Pisum Sativum Mg–chelatase Subunit D (chlD) mRNA, complete cds., XP002149709.
Meizhong Luo and Jon D. Weinstein, 1997, Cloning and Sequencing of a CDNA Encoding the Putattive Mg–Chelatase Subunit D (Accession No. AF014399) from Pea (PGR97–139), XP002149705.
Lucien C. D. Gibson et al., Plant Phys., vol. 111:61–71, 1996, A Putative Mg Chelatase Subunit from *Arabidopsis thaliana* cv C24.
Elisabeth Kruse et al., Plant Mol. Biol., vol. 35:1053–1056, 1997, Isolation and Characterisation of Tobacco (*Nicotiana tabacum*) cDNA Clones Encoding Proteins Involved in Magnesium Chelation into Protoporphyrin IX.
Database EMBL Accession No. AF014051, Aug. 26, 1997, Kurse, E. et al., *Nicotiana tabacum* Mg chelatase subunit (CHlH) mRNA, partial cds., XP002149710.
Database EMBL Accession No. AF014052, Aug. 23, 1997, Kruse et al., *Nicotiana tabacum* Mg Protoporphyrin IX Chelatase (Chl H) mRNA, complete cds., XP002149711.
Database EMBL Accession No. AF014053, Aug. 23, 1997, Kruse, E. et al., *Nicotiana tabacum* Mg protoporphyrin chelatase subunit (Chl I) mRNA, complete cds, XP002149712.
Database EMBL Accession No. U26916, Jun. 16, 1995, Jensen, P.E. et al., Hordeum vulgare protoporphyrin IX Mg–chelatase subunit precursor (Xantha–f) gene, complete cds., XP002149713.
Poul Erik Jensen et al., Mol. Gen. Genet., vol. 250:383–394, 1996, Structural Genes for Mg–chelatase Subunits in Barley: Xantha–f, –g and –h.

(List continued on next page.)

*Primary Examiner*—Phuong T. Bui
(74) *Attorney, Agent, or Firm*—Connolly Bove Lodge & Hutz LLP

(57) ABSTRACT

This invention relates to an isolated nucleic acid fragment encoding a magnesium chelatase subunit. The invention also relates to the construction of a chimeric gene encoding all or a substantial portion of the magnesium chelatase subunit, in sense or antisense orientation, wherein expression of the chimeric gene results in production of altered levels of the magnesium chelatase subunit in a transformed host cell.

11 Claims, 5 Drawing Sheets

OTHER PUBLICATIONS

Database EMBL Accession No. AJ001091, Apr. 15, 1998, Nakayama, M., Glycine Max mRNA for Magnesium Chelatase Subunit, XP002149714.

Masato Nakayama et al., Biochemical and Biophysical Res. Comm., vol. 215(1):1995, Cloning, Subcellular Localization and Expression of CHL1, A Subunit of Magnesium–Chelatase in Soybean.

Database EMBL Accession No. D45857, Feb. 24, 1997, Takamiya, K. Soybean mRNA for Mg Chelatase Subunit (46 kd), complete cds., XP002149715.

Robert D. Willows et al., "heterologous Expression of the Rhodobacter capsulatus BchI, –D, and –H Genes That Encode Magnesium Chelatase Subunits and Characterization of the Reconstituted Enzyme", Journ. of Bio. Chem., vol. 273(51):34206–34213, (1998).

Jutta Papenbrock et al., "Mg–chelatase of tobacco: identification of a Chl D cDNA sequence encoding a third subunit, analysis of the interaction of the three subunits with the yeast two–hybrid system, and reconstitution of the enzyme activity by co–expression of recombinant CHL D, CHL H and CHL I", The Plant Journal, vol. 12(5):981–990, (1997).

Ribo Guo et al., "Magnesium–Chelatase from Developing Pea Leaves", Plant Phys., vol. 116:605–615, (1998).

NCBI General Identifier No. 3913218.

NCBI General Identifier No. 3913240.

NCBI General Identifier No. 6066383.

NCBI General Identifier No. 3059095.

NCBI General Identifier No. 2130042.

Poul Erik Jensen et al., "Structural genes for Mg–chelatase subunits in barley: Xantha–f, –g and –h", Mol. Gen. Genet., vol. 250:383–394, (1996).

NCBI General Identifier No. 7450927.

NCBI General Identifier No. 3334150.

Masato Nakayama et al., "Cloning, Subcellular localization and expression of CHLI, A subunit of magnesium–chelatase in soybean", Biochem and biophys. comm., vol. 215(1):422–428, (1995).

* cited by examiner

```
SEQ ID NO:04  MA----TPTALPTSLPYLPPRRVI----SFPSAAAVSLPVTSRPARLRD-SRLAAAATSAS
SEQ ID NO:12  MGFALAFTASSTCCSNLQSQSLLFAAAALRSKPCLSLCNTYRPKRIRKRSPIVGAQSENG
SEQ ID NO:51  MGFSLTHTPHTTASPNLQLRFHSLLPPSFTSQPFLSHSTFPPKRT---VPKLRAQSENG
              1                                                          60

SEQ ID NO:04  EVLESTNGAVPTAAKDGAWRGYGREYFPLAAVVGQDAIKTALLLGAIDREIGGIAISGKR
SEQ ID NO:12  ALVTSEK---PGTN------YGRQYFPLAAVVGQDAIKTALLLGAIDPGIGGIAISGKR
SEQ ID NO:51  AVLQASEEKLDASN------YGRQYFPLAAVIGQDAIKTALLLGATDPRIGGIAISGRR
              61                                                         120

SEQ ID NO:04  GTAKTVMARGLHAMLPIEVVVGSIANADPNSPDEWEDGLADQIQYDSDGNVKSEIVKTP
SEQ ID NO:12  GTAKTVMARGLHAILPPIEVVVGSIANADPTCPEEWEDGLTECLEYDSAGNIKTRIIKSP
SEQ ID NO:51  GTAKTIMARGMHAILPPIEVVQGSIANADPSCPEEWEDGLYKRVEYDSDGNVKTHIIKSP
              121                                                        180

SEQ ID NO:04  FVQIPLGVTEDRLIGSVDVEASVRSGTTVFQPGLLAEAHRGVLYVDEINLLDDGISNLLL
SEQ ID NO:12  FVQIPLGITEDRLIGSVDVDVEESVKTGTTVFQPGLLAEAHRGVLYVDEINLLEGISNLLL
SEQ ID NO:51  FVQIPLGVTEDRLIGSVDVEESVKTGTTVFQPGLLAEAHRGVLYVDEINLLDEGISNLLL
              181                                                        240

SEQ ID NO:04  NVLTEGVNIVEREGISFRHPCKPLLIATYNPEEGSVREHLLDRIAINLSADLPMSFDDRV
SEQ ID NO:12  NVLSEGVNTVEREGISFKHPCRPLLIATYNPEEGAVREHLLDRIAINLSADLPMSFENRV
SEQ ID NO:51  NVLTEGVNIVEREGISFRHPCRPLLIATYNPDEGSVREHLLDRIAINLSADLPMSFENRV
              241                                                        300
```

FIG. 1A

```
SEQ ID NO:04    ** ****    ** *** *  * * ***   ** *** * *******  ****** *** *******  ** ***
SEQ ID NO:12    EAVDIATRFQESSKEVFKMVEEKTETAKTQIIFAREYLKDVTISTEQLKYLVMEAIRGGC
SEQ ID NO:51    AAVGIATEFQENSSQVFEMVEETDNAKTQIILAREYLKDVTLNRDQLKYLVIEALRGGC
                EAVGIATEFQDNCGQVFKMVDEDTDNAKTQIILAREYLKDVTISKEQLKYLVIEALRGGV
                301                                                      360

SEQ ID NO:04    ************ ****************  ***** ******* * *** *****
SEQ ID NO:12    QGHRAELYAARVAKCLAAMEGREKVFVDDLKKAVELVILPRSILSDNPQDQQQEQPPPPP
SEQ ID NO:51    QGHRAELFAARVAKCLAALEGREKVYVDDLKKAVELVILPRSIITESPPDQQNQPPPPPP
                QGHRAELYAARVAKCLAALEGREKVYVDDLKKAVELVILPRSIITDTPPEQQNQPPPPPP
                361                                                      420

SEQ ID NO:04    **            *          *  *   *     ********************
SEQ ID NO:12    PPPPPEN-QDSSEDQDEEDEDQEEDDEEENEQQDQQIPEEFIFDAEGGLVDDKLLFFAQQA
SEQ ID NO:51    PPQNQESGEEQNEEEQE----DDKDEENEQQQEQLPEEFIFDAEGGLVDEKLLFFAQQA
                PPQNQESNEEQNEEEEQEEEEEDDNDEENEQQQDLPEEFIFDAEGGLVDEKLLFFAQQA
                421                                                      480

SEQ ID NO:04    ***** ************************ ***************  *
SEQ ID NO:12    QRRRGKAGRAKNVIFSEDRGRYIKPMLPKGPVRRLAVDATLRAAAPYQKLRREKERDKTR
SEQ ID NO:51    QRRRGRAGRAKNVIFSEDRGRYIKPMLPKGPVRRLAVDATLRAAAPYQKLRREKDSGNSR
                QRRRGKAGRAKNVIFSEDRGRYIKPMLPKGPVKRLAVDATLRAAAPYQKLRREKDTENRR
                481                                                      540

SEQ ID NO:04    ** *****************************************************
SEQ ID NO:12    KVFVEKTDMRAKRMARKAGALVIFVVDASGSMALNRMQNAKGAALKLLAESYTSRDQVSI
SEQ ID NO:51    KVFVEKTDMRAKRMARKAGALVIFVVDASGSMALNRMQNAKGAALKLLAESYTSRDQVSI
                KVYVEKTDMRAKRMARKAGALVIFVVDASGSMALNRMQNAKGAALKLLAESYTSRDQVSI
                541                                                      600
```

FIG. 1B

```
SEQ ID NO:04    ************************************************************
SEQ ID NO:12    IPFRGDYAEVLLPPSRSIAMARKRLEKLPCGGGSPLAHGLSTAVRVGLNAEKSGDVGRIM
SEQ ID NO:51    IPFRGDAAEVLLPPSRSIAMARKRLERLPCGGGSPLAHGLTTAVRVGLNAEKSGDVGRVM
                IPFRGDSAEVLLPPSRSIAMARKRLERLPCGGGSPLAHGLTTAVRVGLNAEKSGDVGRIM
                601                                                          660

SEQ ID NO:04    ****************  ***  ****      **  ***  ************
SEQ ID NO:12    IVAITDGRANVSLKESTTPEGVAASDAPSLSSQELKDEILEVAGKIYKAGMSLLVIDTEN
SEQ ID NO:51    IVAITDGRANISLKRSTDPEVAAATDAPKPSAQELKDEILEVAGKIYKAGMSLLVIDTEN
                IVAITDGRANISLKRSNDPEAAAASDAPKPTSQELKDEIIEVAAKIYKTGMSLLVIDTEN
                661                                                          720

SEQ ID NO:04    *************************************  **  ****
SEQ ID NO:12    KFVSTGFAKEIARVAQGKYYYLPNASDAVISAATKTALTDLKSS
SEQ ID NO:51    KFVSTGFAKEIARVAQGKYYYLPNASDAVISSATKEALSALKSS
                KFVSTGFAKEIARVAQGKYYYLPNASDAVVSLATREALAALKSS
                721                                          764
```

FIG. 1C

```
                        *             *    *    *  *            *    *    *        *  *
SEQ ID NO:44    MASTFSPTSAARA-----LLPGSTSRPLF--LAASAS--SGRIQPSRKGLDFRRGR--FTV
SEQ ID NO:50    MASAFSPATAAPAASPALFSASTSRPLS--LTAAAAAVSARI-PSRRG--FRRGR--FTV
SEQ ID NO:52    MASALGTSSIAVLPSR-YFSSSSSKPSIHTLSLTSGQNYGRKFYGGIGIHGIKGRAQLSV
                1                                                           60

***               *     **  ******* ******************** ***
SEQ ID NO:44    CNVAAPTAAEQEATASAAKETQRPVYPFAAIVGQDEMKLCLLLNVIDPKIGGVMIMGDRG
SEQ ID NO:50    CNVAAPSATQQEAKAAGAKESQRPVYPFAAIVGQDEMKLCLLLNVIDPKIGGVMIMGDRG
SEQ ID NO:52    TNVATEVNSVEQAQSIASKESQRPVYPFSAIVGQDEMKLCLLLNVIDPKIGGVMIMGDRG
                61                                                          120

************************ *   **  *** **  *** ***          **
SEQ ID NO:44    TGKSTTVRSLVDLLPDIRVVGDLLPDIRVVGDPFNSDPDDPEVMGPEVRQRVLQGDTGLPVTTAIVTMV
SEQ ID NO:50    TGKSTTVRSLVDLLPDIRVVGDPFNSDPDDPEVMGPEVRERVLEGEK-LPVVTAKITMV
SEQ ID NO:52    TGKSTTVRSLVDLLPEIKVVAGDPYNSDPQDPEFMGVEVRERVLQGEE-LSVVLTKINMV
                121                                                         180

****************** ***************     **********************
SEQ ID NO:44    DLPLGATEDRVCGTIDIEKALTEGVKAFEPGLLAKANRGILYVDEVNLLDDHLVDVLLDS
SEQ ID NO:50    DLPLGATEDRVCGTIDIEKALTDGVKAFEPGLLAKANRGILYVDEVNLLDDHLVDVLLDS
SEQ ID NO:52    DLPLGATEDRVCGTIDIEKALTEGVKAFEPGLLAKANRGILYVDEVNLLDDHLVDVLLDS
                181                                                         240
```

FIG. 2A

```
SEQ ID NO:44        ********************  ***  *  ******  ***  ********  **  *  **  *  *
SEQ ID NO:50        AASGWNTVEREGISISHLVGFILMGFVNPEEGEFSPQLLDRFGLQAQVVPFRDPEFRLKI
SEQ ID NO:52        AASGWNTVEREGISISHPARFILIGSGNPEEGELRPQLLDRFGMHAQVGTVRDAELRVKI
                    AASGWNTVEREGISISHPARFILIGSGNPEEGELRPQLLDRFGMHAQVGTVRDAELRVKI
                    241                                                              300

SEQ ID NO:44        *   **   **  ***  ***   **  *   *****  *****  *  *****  *******
SEQ ID NO:50        LEGRLVFDRNPKTFRESYHDEQEKLQQQISSARSNLGAVQIDHDLRVKISKVCSELNVDG
SEQ ID NO:52        VEERARFDRDPKAFRESYLEEQDKLQQQISSARSNLGAVQIDHDLRVKISKVCAELNVDG
                    VEERGRFDKNPKEFRDSYKAEQEKLQQQITSARSVLSSVQIDQDLKVKISKVCAELNVDG
                    301                                                              360

SEQ ID NO:44        ************************  *  ************************  ******
SEQ ID NO:50        LRGDIVTNRAAKALAALKGRDSVTVEDIATVIPNCLRHRLRKDPLESIDSGLLVIEKFYE
SEQ ID NO:52        LRGDIVTNRAAKALAALKGRDTVTVEDIATVIPNCLRHRLRKDPLESIDSGLLVVEKFYE
                    LRGDIVTNRAAKALAALKGRDNVSAEDIATVIPNCLRHRLRKDPLESIDSGLLVTEKFYE
                    361                                                              420

SEQ ID NO:44        **
SEQ ID NO:50        VFS
SEQ ID NO:52        VFT
                    VFS
                    421
```

FIG. 2B

SEQUENCE LISTING

```
<160> NUMBER OF SEQ ID NOS: 54

<210> SEQ ID NO 1
<211> LENGTH: 432
<212> TYPE: DNA
<213> ORGANISM: Zea mays
<220> FEATURE:
<221> NAME/KEY: unsure
<222> LOCATION: (2)
<221> NAME/KEY: unsure
<222> LOCATION: (10)
<221> NAME/KEY: unsure
<222> LOCATION: (19)
<221> NAME/KEY: unsure
<222> LOCATION: (21)
<221> NAME/KEY: unsure
<222> LOCATION: (35)

<400> SEQUENCE: 1
anccaaaaan tgcgtcacna ncctgcgttg gtccngatgc tatcaaaact gctgctgctg      60
```

```
cttggggcga ttgatcgtga gatcggaggc attgccatct cagggaagcg tgggacggca      120
aagacagtga tggctcgtgg tttgcatgct atgcttccac ccattgaagt ggtggttggt      180
tccattgcaa atgctgaccc taactcccct gacgaatggg aggatggttt agctgatcaa      240
atacagtatg actctgatgg taatgtcaaa tccgagattg tcaaaacacc ttttgtgcag      300
attccacttg gtgtgacgga ggataggctc attggatcag ttgatgttga agcatctgtg      360
agatcaggga ctactgtatt caacctggct cttgctgaac ataaggtg tcttatgtga        420 tgaataacta tg                                                          432

<210> SEQ ID NO 2
<211> LENGTH: 116
<212> TYPE: PRT
<213> ORGANISM: Zea mays

<400> SEQUENCE: 2

Lys Leu Leu Leu Leu Gly Ala Ile Asp Arg Glu Ile Gly Gly Ile
  1               5                  10                  15

Ala Ile Ser Gly Lys Arg Gly Thr Ala Lys Thr Val Met Ala Arg Gly
                 20                  25                  30

Leu His Ala Met Leu Pro Pro Ile Glu Val Val Gly Ser Ile Ala
             35                  40                  45

Asn Ala Asp Pro Asn Ser Pro Asp Glu Trp Glu Asp Gly Leu Ala Asp
     50                  55                  60

Gln Ile Gln Tyr Asp Ser Asp Gly Asn Val Lys Ser Glu Ile Val Lys
 65                  70                  75                  80

Thr Pro Phe Val Gln Ile Pro Leu Gly Val Thr Glu Asp Arg Leu Ile
                 85                  90                  95

Gly Ser Val Asp Val Glu Ala Ser Val Arg Ser Gly Thr Thr Val Phe
            100                 105                 110

Asn Leu Ala Leu
        115

<210> SEQ ID NO 3
<211> LENGTH: 2513
<212> TYPE: DNA
<213> ORGANISM: Zea mays

<400> SEQUENCE: 3
cggcacgagc catggcgacg cccaccgcgc tccccacctc actcccctac ctcccgcccc       60
gccgcgtcat ctcattccca tccgccgccg ccgtctccct cccgtcacc tcccgccccg      120 cccggctgcg ggattcccgc ctcgcggccg gcaacctc ggcctccgag gtcctcgagt       180
ccaccaacgg cgccgtcccc actgcggcca aggacggcgc gtggcgcggg tatgggaggg      240
agtacttccc cctggctgcc gtcgttgggc aggatgctat caaaactgct ctgctgcttg      300 ggcgattga tcgtgagatc ggaggcattg ccatctcagg gaagcgtggg acggcaaaga      360
cagtgatggc tcgtggtttg catgctatgc ttccacccat tgaagtggtg ttggttcca      420 ttgcaaatgc tgaccctaac tcccctgacg aatgggagga tggtttagct gatcaaatac      480
agtatgactc tgatggtaat gtcaaatccg agattgtcaa acaccttttt gtgcagattc      540
cacttggtgt gacggaggat aggctcattg gatcagttga tgttgaagca tctgtgagat      600
cagggactac tgtatttcaa cctggtcttc ttgctgaagc atagaggt gttctttatg      660 ttgatgaaat aaatctattg gatgatggca taagcaatct acttctgaat gtcttgacgg      720
agggagttaa cattgtggaa agagagggca ttagctttcg ccatccctgc aaaccacttc      780
```

```
taattgctac ttacaatcca gaggaagggt ctgtacgtga acacttgctt gatcgtattg    840
caattaattt aagtgctgat cttccaatga gttttgatga ccgcgttgaa gcagtggata    900
ttgcaacacg gtttcaggag tctagcaaag aagtttttcaa aatggtggaa gaaaaaactg    960
aaactgcaaa aactcagata attttttgcaa gagagtatct gaaggatgtt actattagca   1020
cagagcagct caaatatctt gtcatggaag ctatacgagg tggctgtcag gggcatcgtg   1080
ctgagttgta tgctgctcga gttgcaaaat gtctagctgc tatggaagga cgtgaaaaag   1140
tatttgtgga tgacctcaag aaagctgtag agctagtcat tctacctcgc tccatcctat   1200
ctgataatcc acaggatcag cagcaagagc aaccaccccc accccgcca ccaccctc     1260 cagaaaatca agattcttca gaagaccaag atgaggaaga cgaagaccaa gaggatgatg   1320
aagaagaaaa tgaacaacaa gaccaacaga tacctgagga gttcatattt gatgctgaag   1380
gtggtttagt agatgacaaa cttctttttct ttgcccagca agcacagaga cgacgtggaa   1440
aagctgggcg agcaaagaat gtcatcttct cagaagatag gggccgttac ataaagccta   1500
tgcttcctaa gggtccagta aggaggttag ctgttgatgc cacgcttaga gcagctgcac   1560
cataccaaaa actgcgcaga gagaaagaac gtgacaaaac aagaaaggtt tttgttgaaa   1620
agactgacat gagagccaaa agaatggctc gaaaagcagg tgctctagtc atatttgttg   1680
tggacgctag tggtagcatg gctctgaatc gtatgcagaa tgctaaaggt gcggcgttga   1740
agttgcttgc agaaagctac accagcagag atcaggtttc aattattcct tttcgtggag   1800
attatgctga ggttttgctt ccaccatcaa gatctatagc aatggcccgg aaacgtcttg   1860
agaagctacc atgtggtggt ggttctcctt tagctcatgg cctaagtaca gctgtcagag   1920
tgggtctgaa tgctgaaaag agtggcgatg ttgggcgtat catgattgtt gcaatcaccg   1980
atggaagagc taatgtatca ctgaaggaat caactacccc agaaggtgtt gctgcttcag   2040
atgcgccaag cctttcttct caagaactga aggacgagat acttgaggtg gctggcaaaa   2100
tatacaaggc aggaatgtcc cttcttgtca tcgacactga gaacaagttt gtatccacgg   2160
gatttgccaa ggaaattgca agggttgccc aggggaaata ttattacctc cctaatgctt   2220
cggatgctgt aatttctgct gccaccaaga ccgccctgac agacttgaag agctcatgat   2280
tttgcagcag cggcacccgt tttctgtacc ttttgatagg ggtggtgaac cttcattcat   2340
gcagtagttt ttgtgtaggc ctctacaatg acagggggaa acaaacccga gcatggcatc   2400
gtgtaaagtg ttaaggtcca atggcctcct gtccacgttt ggcgatgtaa atcctccgta   2460
acatagcttg aaccattgag tgtcacgtag tgccatggct agcagttaaa agt           2513
```

<210> SEQ ID NO 4
<211> LENGTH: 755
<212> TYPE: PRT
<213> ORGANISM: Zea mays

<400> SEQUENCE: 4

```
Met Ala Thr Pro Thr Ala Leu Pro Thr Ser Leu Pro Tyr Leu Pro Pro
 1               5                  10                  15

Arg Arg Val Ile Ser Phe Pro Ser Ala Ala Val Ser Leu Pro Val
            20                  25                  30

Thr Ser Arg Pro Ala Arg Leu Arg Asp Ser Arg Leu Ala Ala Ala Ala
        35                  40                  45

Thr Ser Ala Ser Glu Val Leu Glu Ser Thr Asn Gly Ala Val Pro Thr
    50                  55                  60
```

-continued

```
Ala Ala Lys Asp Gly Ala Trp Arg Gly Tyr Gly Arg Glu Tyr Phe Pro
 65                  70                  75                  80

Leu Ala Ala Val Val Gly Gln Asp Ala Ile Lys Thr Ala Leu Leu Leu
                 85                  90                  95

Gly Ala Ile Asp Arg Glu Ile Gly Gly Ile Ala Ile Ser Gly Lys Arg
            100                 105                 110

Gly Thr Ala Lys Thr Val Met Ala Arg Gly Leu His Ala Met Leu Pro
        115                 120                 125

Pro Ile Glu Val Val Gly Ser Ile Ala Asn Ala Asp Pro Asn Ser
    130                 135                 140

Pro Asp Glu Trp Glu Asp Gly Leu Ala Asp Gln Ile Gln Tyr Asp Ser
145                 150                 155                 160

Asp Gly Asn Val Lys Ser Glu Ile Val Lys Thr Pro Phe Val Gln Ile
                165                 170                 175

Pro Leu Gly Val Thr Glu Asp Arg Leu Ile Gly Ser Val Asp Val Glu
            180                 185                 190

Ala Ser Val Arg Ser Gly Thr Thr Val Phe Gln Pro Gly Leu Leu Ala
        195                 200                 205

Glu Ala His Arg Gly Val Leu Tyr Val Asp Glu Ile Asn Leu Leu Asp
    210                 215                 220

Asp Gly Ile Ser Asn Leu Leu Asn Val Leu Thr Glu Gly Val Asn
225                 230                 235                 240

Ile Val Glu Arg Glu Gly Ile Ser Phe Arg His Pro Cys Lys Pro Leu
                245                 250                 255

Leu Ile Ala Thr Tyr Asn Pro Glu Glu Gly Ser Val Arg Glu His Leu
            260                 265                 270

Leu Asp Arg Ile Ala Ile Asn Leu Ser Ala Asp Leu Pro Met Ser Phe
        275                 280                 285

Asp Asp Arg Val Glu Ala Val Asp Ile Ala Thr Arg Phe Gln Glu Ser
    290                 295                 300

Ser Lys Glu Val Phe Lys Met Val Glu Lys Thr Glu Thr Ala Lys
305                 310                 315                 320

Thr Gln Ile Ile Phe Ala Arg Glu Tyr Leu Lys Asp Val Thr Ile Ser
                325                 330                 335

Thr Glu Gln Leu Lys Tyr Leu Val Met Glu Ala Ile Arg Gly Gly Cys
            340                 345                 350

Gln Gly His Arg Ala Glu Leu Tyr Ala Ala Arg Val Ala Lys Cys Leu
        355                 360                 365

Ala Ala Met Glu Gly Arg Glu Lys Val Phe Val Asp Asp Leu Lys Lys
    370                 375                 380

Ala Val Glu Leu Val Ile Leu Pro Arg Ser Ile Leu Ser Asp Asn Pro
385                 390                 395                 400

Gln Asp Gln Gln Gln Glu Gln Pro Pro Pro Pro Pro Pro Pro Pro
                405                 410                 415

Pro Glu Asn Gln Asp Ser Ser Glu Asp Gln Asp Glu Asp Glu Asp
            420                 425                 430

Gln Glu Asp Asp Glu Glu Glu Asn Glu Gln Gln Asp Gln Gln Ile Pro
        435                 440                 445

Glu Glu Phe Ile Phe Asp Ala Glu Gly Gly Leu Val Asp Asp Lys Leu
    450                 455                 460

Leu Phe Phe Ala Gln Gln Ala Gln Arg Arg Gly Lys Ala Gly Arg
465                 470                 475                 480

Ala Lys Asn Val Ile Phe Ser Glu Asp Arg Gly Arg Tyr Ile Lys Pro
```

```
                     485                 490                 495
Met Leu Pro Lys Gly Pro Val Arg Arg Leu Ala Val Asp Ala Thr Leu
                500                 505                 510

Arg Ala Ala Pro Tyr Gln Lys Leu Arg Arg Glu Lys Glu Arg Asp
            515                 520                 525

Lys Thr Arg Lys Val Phe Val Glu Lys Thr Asp Met Arg Ala Lys Arg
        530                 535                 540

Met Ala Arg Lys Ala Gly Ala Leu Val Ile Phe Val Val Asp Ala Ser
545                 550                 555                 560

Gly Ser Met Ala Leu Asn Arg Met Gln Asn Ala Lys Gly Ala Ala Leu
                565                 570                 575

Lys Leu Leu Ala Glu Ser Tyr Thr Ser Arg Asp Gln Val Ser Ile Ile
                580                 585                 590

Pro Phe Arg Gly Asp Tyr Ala Glu Val Leu Leu Pro Pro Ser Arg Ser
            595                 600                 605

Ile Ala Met Ala Arg Lys Arg Leu Glu Lys Leu Pro Cys Gly Gly Gly
        610                 615                 620

Ser Pro Leu Ala His Gly Leu Ser Thr Ala Val Arg Val Gly Leu Asn
625                 630                 635                 640

Ala Glu Lys Ser Gly Asp Val Gly Arg Ile Met Ile Val Ala Ile Thr
                645                 650                 655

Asp Gly Arg Ala Asn Val Ser Leu Lys Glu Ser Thr Thr Pro Glu Gly
            660                 665                 670

Val Ala Ala Ser Asp Ala Pro Ser Leu Ser Ser Gln Glu Leu Lys Asp
        675                 680                 685

Glu Ile Leu Glu Val Ala Gly Lys Ile Tyr Lys Ala Gly Met Ser Leu
        690                 695                 700

Leu Val Ile Asp Thr Glu Asn Lys Phe Val Ser Thr Gly Phe Ala Lys
705                 710                 715                 720

Glu Ile Ala Arg Val Ala Gln Gly Lys Tyr Tyr Tyr Leu Pro Asn Ala
                725                 730                 735

Ser Asp Ala Val Ile Ser Ala Ala Thr Lys Thr Ala Leu Thr Asp Leu
            740                 745                 750

Lys Ser Ser
        755

<210> SEQ ID NO 5
<211> LENGTH: 478
<212> TYPE: DNA
<213> ORGANISM: Oryza sativa
<220> FEATURE:
<221> NAME/KEY: unsure
<222> LOCATION: (244)
<221> NAME/KEY: unsure
<222> LOCATION: (441)
<221> NAME/KEY: unsure
<222> LOCATION: (452)
<221> NAME/KEY: unsure
<222> LOCATION: (478)

<400> SEQUENCE: 5
gtgaaaaagt atatgtggat gaccttaaga aagctgtaga gctagttatt ctacctcgat      60
caatcctatc tgataaccca caggagcagc aagaccaaca acctcctcca cccccaccgc     120 cacccccctcc acaagatcaa gattctcaag aagatcaaga tgaagacgag gaagaggacc    180
aagaggacga tgatgaagaa atgaacagc aggaccagca gataccgtag gagttcattt      240
ttgntgctga aggtggtata gtagatgaga agctccttt ctttgctcag caagctcaaa      300
```

```
gacggcgagg gaaagctgga cgagcaaaga atctcatatt ctcatctgat agggacgat    360 acataggttc tatgcttccc aagggtccaa taaggagggt tagctgttga tgccacactt   420
cgagcagctg caccataccg naaactgagg gngagagaaa agatctgaca agacaagn     478
```

<210> SEQ ID NO 6
<211> LENGTH: 149
<212> TYPE: PRT
<213> ORGANISM: Oryza sativa
<220> FEATURE:
<221> NAME/KEY: UNSURE
<222> LOCATION: (81)
<221> NAME/KEY: UNSURE
<222> LOCATION: (146)

<400> SEQUENCE: 6

```
Glu Lys Val Tyr Val Asp Asp Leu Lys Lys Ala Val Glu Leu Val Ile
 1               5                  10                  15

Leu Pro Arg Ser Ile Leu Ser Asp Asn Pro Gln Glu Gln Gln Asp Gln
            20                  25                  30

Gln Pro Pro Pro Pro Pro Pro Pro Pro Gln Asp Gln Asp Ser
        35                  40                  45

Gln Glu Asp Gln Asp Glu Asp Glu Glu Asp Gln Glu Asp Asp Asp
     50                  55                  60

Glu Glu Asn Glu Gln Gln Asp Gln Gln Ile Pro Glu Glu Phe Ile Phe
65                  70                  75                  80

Xaa Ala Glu Gly Gly Ile Val Asp Glu Lys Leu Leu Phe Phe Ala Gln
                85                  90                  95

Gln Ala Gln Arg Arg Arg Gly Lys Ala Gly Arg Ala Lys Asn Leu Ile
            100                 105                 110

Phe Ser Ser Asp Arg Gly Arg Tyr Ile Gly Ser Met Leu Pro Lys Gly
        115                 120                 125

Pro Ile Arg Arg Leu Ala Val Asp Ala Thr Leu Arg Ala Ala Ala Pro
    130                 135                 140

Tyr Xaa Lys Leu Arg
145
```

<210> SEQ ID NO 7
<211> LENGTH: 1477
<212> TYPE: DNA
<213> ORGANISM: Oryza sativa

<400> SEQUENCE: 7

```
gcacgaggtg aaaaagtata tgtggatgac cttaagaaag ctgtagagct agttattcta    60
cctcgatcaa tcctatctga taacccacag gagcagcaag accaacaacc tcctccaccc   120
ccaccgccac cccctccaca agatcaagat tctcaagaag atcaagatga agacgaggaa   180
gaggaccaag aggacgatga tgaagaaaat gaacagcagg accagcagat acctgaggag   240 ttcattttg atgctgaagg tggtatagta gatgagaagc tccttttctt tgctcagcaa    300
gctcaaagac ggcgagggaa agctggacga gcaaagaatc tcatattctc atctgatagg   360
ggacgataca taggttctat gcttcccaag ggtccaataa ggaggttagc tgttgatgcc   420 acattcgag cagctgcacc ataccagaaa ctgaggagag agaaagatcg tgacaagaca    480
agaaaggttt ttgttgaaaa aactgacatg agagccaaaa gaatggctcg aaaagcaggc   540
gcactggtca tatttgttgt ggatgctagc ggtagcatgg ctctgaatcg catgcagaat   600
gcgaaaggtg cagcattaaa gttgcttgca gaaagctaca agcagaga tcaggtttca     660
```

-continued

```
atcattccat tttcgtggaga ttttgctgag gttcttcttc caccttcaag atccatagca      720
atggcccgca atcgtcttga gaagctacca tgtggtggcg gttctccttt agctcacggc      780
cttagcacag ctgtcagagt gggtttgaat gctgaaaaga gcggtgatgt tggacgtatc      840
atgattgttg caataccga tggaagagct aatgtgtcac tgaagaaatc gactgaccca      900
gaagccactt cagatgctcc aagaccttct tctcaagaat taaaggatga gatacttgag      960
gtggctggca aaatatacaa ggctggaatt tcacttcttg ttattgatac cgagaacaag     1020
tttgtatcca caggatttgc caaggaaatt gcaagggtcg cccaaggtaa atactattac     1080
ctgccgaatg cttcagacgc tgttatttcc gccgccacca agactgcact ctcggacctg     1140
aagagttcgt gatcctggag agcgttttac cttcagataa tgagtggttt ttaccttta      1200 ccttgtttgg tgcagcagtg tccatgtttc gtgtaacttt gggacgtttc ggctgtgata     1260
accaattttg gcataggatt tttaccgtga gagttgaat tcgggcgtag caccgtgtaa      1320
agaatcatat aatccctctt ctgtctaaat aattggccat gtaaatatgg tgttattgcg     1380
tacagttcta agtaataata acattcataa tttatgtgaa aaaaaaaaaa aaaaaaaaa      1440 aaaaaaaaaa aaaaaaaaaa aaactcgaga ctagttc                              1477
```

<210> SEQ ID NO 8
<211> LENGTH: 383
<212> TYPE: PRT
<213> ORGANISM: Oryza sativa

<400> SEQUENCE: 8

```
Ala Arg Gly Glu Lys Val Tyr Val Asp Asp Leu Lys Lys Ala Val Glu
  1               5                  10                  15

Leu Val Ile Leu Pro Arg Ser Ile Leu Ser Asp Asn Pro Gln Glu Gln
             20                  25                  30

Gln Asp Gln Gln Pro Pro Pro Pro Pro Pro Pro Pro Pro Gln Asp
         35                  40                  45

Gln Asp Ser Gln Glu Asp Gln Asp Glu Asp Glu Glu Asp Gln Glu
     50                  55                  60

Asp Asp Asp Glu Glu Asn Glu Gln Gln Asp Gln Gln Ile Pro Glu Glu
 65                  70                  75                  80

Phe Ile Phe Asp Ala Glu Gly Gly Ile Val Asp Glu Lys Leu Leu Phe
                 85                  90                  95

Phe Ala Gln Gln Ala Gln Arg Arg Arg Gly Lys Ala Gly Arg Ala Lys
            100                 105                 110

Asn Leu Ile Phe Ser Ser Asp Arg Gly Arg Tyr Ile Gly Ser Met Leu
        115                 120                 125

Pro Lys Gly Pro Ile Arg Arg Leu Ala Val Asp Ala Thr Leu Arg Ala
    130                 135                 140

Ala Ala Pro Tyr Gln Lys Leu Arg Arg Glu Lys Asp Arg Asp Lys Thr
145                 150                 155                 160

Arg Lys Val Phe Val Glu Lys Thr Asp Met Arg Ala Lys Arg Met Ala
                165                 170                 175

Arg Lys Ala Gly Ala Leu Val Ile Phe Val Val Asp Ala Ser Gly Ser
            180                 185                 190

Met Ala Leu Asn Arg Met Gln Asn Ala Lys Gly Ala Ala Leu Lys Leu
        195                 200                 205

Leu Ala Glu Ser Tyr Thr Ser Arg Asp Gln Val Ser Ile Ile Pro Phe
    210                 215                 220
```

Arg Gly Asp Phe Ala Glu Val Leu Leu Pro Pro Ser Arg Ser Ile Ala
225                 230                 235                 240

Met Ala Arg Asn Arg Leu Glu Lys Leu Pro Cys Gly Gly Ser Pro
                245                 250                 255

Leu Ala His Gly Leu Ser Thr Ala Val Arg Val Gly Leu Asn Ala Glu
                260                 265                 270

Lys Ser Gly Asp Val Gly Arg Ile Met Ile Val Ala Ile Thr Asp Gly
                275                 280                 285

Arg Ala Asn Val Ser Leu Lys Lys Ser Thr Asp Pro Glu Ala Thr Ser
290                 295                 300

Asp Ala Pro Arg Pro Ser Ser Gln Glu Leu Lys Asp Glu Ile Leu Glu
305                 310                 315                 320

Val Ala Gly Lys Ile Tyr Lys Ala Gly Ile Ser Leu Leu Val Ile Asp
                325                 330                 335

Thr Glu Asn Lys Phe Val Ser Thr Gly Phe Ala Lys Glu Ile Ala Arg
                340                 345                 350

Val Ala Gln Gly Lys Tyr Tyr Tyr Leu Pro Asn Ala Ser Asp Ala Val
                355                 360                 365

Ile Ser Ala Ala Thr Lys Thr Ala Leu Ser Asp Leu Lys Ser Ser
370                 375                 380

<210> SEQ ID NO 9
<211> LENGTH: 398
<212> TYPE: DNA
<213> ORGANISM: Glycine max

<400> SEQUENCE: 9
aatgggtttc gctttggcat tcacagcttc ttctacttgc tgctcaaatc tacaatctca    60
gtctctgtta ttcgctgctg ctgcattgag atcaaaaccg tgtctctctc tctgcaacac   120
ttatcgaccc aaacgcattc ggaagcgttc tccaattgtt ggcgctcaat ctgaaaacgg   180
agctctcgtt acttccgaga agcctggcac taattacgga agacaatact tccccctcgc   240
tgctgttgta ggccaagatg ctataaaaac tgctcttttta cttggggcca ttgaccctgg   300
gattggagga attgccatat caggaaagcg aggaactgcc aaaactgtaa tggcacgtgg   360
actgcatgca atactgcctc ctattgaagt agtagtag                            398

<210> SEQ ID NO 10
<211> LENGTH: 131
<212> TYPE: PRT
<213> ORGANISM: Glycine max

<400> SEQUENCE: 10

Met Gly Phe Ala Leu Ala Phe Thr Ala Ser Ser Thr Cys Cys Ser Asn
1               5                   10                  15

Leu Gln Ser Gln Ser Leu Leu Phe Ala Ala Ala Leu Arg Ser Lys
                20                  25                  30

Pro Cys Leu Ser Leu Cys Asn Thr Tyr Arg Pro Lys Arg Ile Arg Lys
                35                  40                  45

Arg Ser Pro Ile Val Gly Ala Gln Ser Glu Asn Gly Ala Leu Val Thr
    50                  55                  60

Ser Glu Lys Pro Gly Thr Asn Tyr Gly Arg Gln Tyr Phe Pro Leu Ala
65                  70                  75                  80

Ala Val Val Gly Gln Asp Ala Ile Lys Thr Ala Leu Leu Leu Gly Ala
                85                  90                  95

Ile Asp Pro Gly Ile Gly Gly Ile Ala Ile Ser Gly Lys Arg Gly Thr

```
                 100                  105                  110
Ala Lys Thr Val Met Ala Arg Gly Leu His Ala Ile Leu Pro Pro Ile
        115                  120                  125
Glu Val Val
    130

<210> SEQ ID NO 11
<211> LENGTH: 2481
<212> TYPE: DNA
<213> ORGANISM: Glycine max

<400> SEQUENCE: 11
gcacgagaat gggtttcgct ttggcattca cagcttcttc tacttgctgc tcaaatctac      60
aatctcagtc tctgttattc gctgctgctg cattgagatc aaaaccgtgt ctctctctct     120
gcaacactta tcgacccaaa cgcattcgga agcgttctcc aattgttggc gctcaatctg     180
aaaacggagc tctcgttact tccgagaagc ctggcactaa ttacggaaga caatacttcc     240
ccctcgctgc tgttgtaggc caagatgcta taaaaactgc tcttttactt ggggccattg     300
accctgggat tggaggaatt gccatatcag gaaagcgagg aactgccaaa actgtaatgg     360
cacgtggact gcatgcaata ctgcctccta ttgaagtagt agtaggttcc atagccaatg     420
cggatccgac ctgcccagaa gagtgggaag atggtcttac agaatgcctg gaatatgatt     480
ctgctggaaa tattaaaact cgtattatca agtctccctt tgttcagatt cctcttggaa     540
tcacggagga cagactcatt ggatcggttg atgttgagga gtctgtgaaa acaggcacaa     600
ctgttttcca gccaggcttg cttgcagaag ctcatagagg tgttttatat gttgatgaaa     660
ttaatctttt ggatgagggt atcagtaatt tgctccttaa tgtattgagt gaaggagtaa     720
atactgttga agagaggggg atcagtttca agcacccttg caggcccctt ctcattgcca     780
cctataaccc agaagagggt gctgttcgtg aacatctgct ggaccgcatt gcgattaatt     840
taagtgcaga tcttccaatg agttttgaaa accgtgttgc agctgttgga attgccacag     900
agtttcagga gaacagtagc caagtatttg agatggtcga gaggaaaca gacaatgcaa     960
aaactcagat catcttggcc agagagtatc taaagatgt tactctgaac agagatcaat    1020
taaaatacct ggttattgaa gctttacggg gtggttgcca aggacataga gctgagctat    1080
ttgctgcccg tgttgcaaag tgcttagctg ctctggaggg acgggaaaag gtttatgtgg    1140
atgacctaaa aaaagctgta gaattggtca ttctaccccg gtcaatcatt actgagagcc    1200
caccagatca acaaaatcag cctcccccc ctccacctcc tccacaaaat caagaatcag    1260
gcgaagaaca gaatgaagag gaagaacaag aggatgacaa ggatgaagag aatgaacaac    1320
agcaagaaca attacctgaa gagtttatct ttgatgctga aggtggcttg gtagatgaaa    1380
aactcctctt ctttgcccag caagcacaga gacgccgcgg gagggctgga agggcaaaaa    1440
atgtaatatt ttcagaggat agaggccgat acatcaagcc aatgcttcca aagggccctg    1500
taaagagatt agctgtagat gcaaccctta gctgctgc accttatcaa aaattgcgaa    1560
gggaaaaaga ctcaggaaac agtagaaaag tatttgtgga aaaacggac atgagggcaa    1620
agagaatggc acgtaaggca ggagcattgg tgatatttgt ggttgatgca gtggaagca    1680
tggcattgaa caggatgcag aatgcaaaag gtgcagcact taagcttctg gctgaaagtt    1740
atacaagcag ggatcaggtc tctataattc cattccgtgg agatgcagct gaagttcttc    1800
tgccaccttc tagatcaatt gcaatggcaa ggaaacgtct tgagaggctt ccatgtggtg    1860
gagggtcccc acttgctcat ggtcttacaa cggctgttag agttggatta aatgcggaga    1920
```

-continued

```
aaagtggtga cgttggacgt gtgatgattg ttgcaatcac tgatggcaga gccaatatat    1980
cattgaaaag gtcgactgac cctgaagttg ccgcagctac tgatgcccca aaaccttcag    2040
cacaagaatt gaaggatgaa attcttgagg tggctgggaa gatttataaa gcaggaatgt    2100
ctctccttgt catcgacact gaaaataagt ttgtctcaac gggtttcgcc aaggagattg    2160
ctagagttgc ccaaggcaag tattattatc tgccaaatgc ttcagacgct gttatctcat    2220
cggcaacaaa ggaagcttta tcagctttga aagttcatg aaaccttgta aaataaagc     2280 agtcaaacat cacttccccc tttggtcgta aatgttaatg taaatcatgc aaactatgtt    2340
atgatgggaa gaacgcatgt tgtaataacc aggagcaatt ttgaatcata ccaatgctaa    2400 caaccatag acatgataat gatcagtgta aaaaaaaaa aaaaaaaaa acaaaaaaaa      2460 aaaaaaaaaa aaaaaaaaa a                                              2481
```

<210> SEQ ID NO 12
<211> LENGTH: 750
<212> TYPE: PRT
<213> ORGANISM: Glycine max

<400> SEQUENCE: 12

```
Met Gly Phe Ala Leu Ala Phe Thr Ala Ser Ser Thr Cys Cys Ser Asn
  1               5                  10                  15

Leu Gln Ser Gln Ser Leu Leu Phe Ala Ala Ala Leu Arg Ser Lys
             20                  25                  30

Pro Cys Leu Ser Leu Cys Asn Thr Tyr Arg Pro Lys Arg Ile Arg Lys
         35                  40                  45

Arg Ser Pro Ile Val Gly Ala Gln Ser Glu Asn Gly Ala Leu Val Thr
     50                  55                  60

Ser Glu Lys Pro Gly Thr Asn Tyr Gly Arg Gln Tyr Phe Pro Leu Ala
 65                  70                  75                  80

Ala Val Val Gly Gln Asp Ala Ile Lys Thr Ala Leu Leu Gly Ala
                 85                  90                  95

Ile Asp Pro Gly Ile Gly Ile Ala Ile Ser Gly Lys Arg Gly Thr
            100                 105                 110

Ala Lys Thr Val Met Ala Arg Gly Leu His Ala Ile Leu Pro Pro Ile
        115                 120                 125

Glu Val Val Gly Ser Ile Ala Asn Ala Asp Pro Thr Cys Pro Glu
    130                 135                 140

Glu Trp Glu Asp Gly Leu Thr Glu Cys Leu Glu Tyr Asp Ser Ala Gly
145                 150                 155                 160

Asn Ile Lys Thr Arg Ile Ile Lys Ser Pro Phe Val Gln Ile Pro Leu
                165                 170                 175

Gly Ile Thr Glu Asp Arg Leu Ile Gly Ser Val Asp Val Glu Glu Ser
            180                 185                 190

Val Lys Thr Gly Thr Thr Val Phe Gln Pro Gly Leu Leu Ala Glu Ala
        195                 200                 205

His Arg Gly Val Leu Tyr Val Asp Glu Ile Asn Leu Leu Asp Glu Gly
    210                 215                 220

Ile Ser Asn Leu Leu Leu Asn Val Leu Ser Glu Gly Val Asn Thr Val
225                 230                 235                 240

Glu Arg Glu Gly Ile Ser Phe Lys His Pro Cys Arg Pro Leu Leu Ile
                245                 250                 255

Ala Thr Tyr Asn Pro Glu Glu Gly Ala Val Arg Glu His Leu Leu Asp
            260                 265                 270
```

-continued

```
Arg Ile Ala Ile Asn Leu Ser Ala Asp Leu Pro Met Ser Phe Glu Asn
            275                 280                 285

Arg Val Ala Ala Val Gly Ile Ala Thr Glu Phe Gln Glu Asn Ser Ser
            290                 295                 300

Gln Val Phe Glu Met Val Glu Glu Thr Asp Asn Ala Lys Thr Gln
305                 310                 315                 320

Ile Ile Leu Ala Arg Glu Tyr Leu Lys Asp Val Thr Leu Asn Arg Asp
                325                 330                 335

Gln Leu Lys Tyr Leu Val Ile Glu Ala Leu Arg Gly Gly Cys Gln Gly
            340                 345                 350

His Arg Ala Glu Leu Phe Ala Ala Arg Val Ala Lys Cys Leu Ala Ala
            355                 360                 365

Leu Glu Gly Arg Glu Lys Val Tyr Val Asp Asp Leu Lys Lys Ala Val
    370                 375                 380

Glu Leu Val Ile Leu Pro Arg Ser Ile Ile Thr Glu Ser Pro Pro Asp
385                 390                 395                 400

Gln Gln Asn Gln Pro Pro Pro Pro Pro Pro Gln Asn Gln Glu
                405                 410                 415

Ser Gly Glu Glu Gln Asn Glu Glu Glu Gln Glu Asp Asp Lys Asp
            420                 425                 430

Glu Glu Asn Glu Gln Gln Glu Gln Leu Pro Glu Glu Phe Ile Phe
    435                 440                 445

Asp Ala Glu Gly Gly Leu Val Asp Glu Lys Leu Leu Phe Phe Ala Gln
    450                 455                 460

Gln Ala Gln Arg Arg Arg Gly Arg Ala Gly Arg Ala Lys Asn Val Ile
465                 470                 475                 480

Phe Ser Glu Asp Arg Gly Arg Tyr Ile Lys Pro Met Leu Pro Lys Gly
                485                 490                 495

Pro Val Lys Arg Leu Ala Val Asp Ala Thr Leu Arg Ala Ala Ala Pro
            500                 505                 510

Tyr Gln Lys Leu Arg Arg Glu Lys Asp Ser Gly Asn Ser Arg Lys Val
            515                 520                 525

Phe Val Glu Lys Thr Asp Met Arg Ala Lys Arg Met Ala Arg Lys Ala
    530                 535                 540

Gly Ala Leu Val Ile Phe Val Val Asp Ala Ser Gly Ser Met Ala Leu
545                 550                 555                 560

Asn Arg Met Gln Asn Ala Lys Gly Ala Ala Leu Lys Leu Leu Ala Glu
                565                 570                 575

Ser Tyr Thr Ser Arg Asp Gln Val Ser Ile Ile Pro Phe Arg Gly Asp
            580                 585                 590

Ala Ala Glu Val Leu Leu Pro Pro Ser Arg Ser Ile Ala Met Ala Arg
            595                 600                 605

Lys Arg Leu Glu Arg Leu Pro Cys Gly Gly Ser Pro Leu Ala His
    610                 615                 620

Gly Leu Thr Thr Ala Val Arg Val Gly Leu Asn Ala Glu Lys Ser Gly
625                 630                 635                 640

Asp Val Gly Arg Val Met Ile Val Ala Ile Thr Asp Gly Arg Ala Asn
                645                 650                 655

Ile Ser Leu Lys Arg Ser Thr Asp Pro Glu Val Ala Ala Thr Asp
            660                 665                 670

Ala Pro Lys Pro Ser Ala Gln Glu Leu Lys Asp Glu Ile Leu Glu Val
    675                 680                 685
```

```
Ala Gly Lys Ile Tyr Lys Ala Gly Met Ser Leu Leu Val Ile Asp Thr
    690                 695                 700

Glu Asn Lys Phe Val Ser Thr Gly Phe Ala Lys Glu Ile Ala Arg Val
705                 710                 715                 720

Ala Gln Gly Lys Tyr Tyr Tyr Leu Pro Asn Ala Ser Asp Ala Val Ile
                    725                 730                 735

Ser Ser Ala Thr Lys Glu Ala Leu Ser Ala Leu Lys Ser Ser
                740                 745                 750

<210> SEQ ID NO 13
<211> LENGTH: 511
<212> TYPE: DNA
<213> ORGANISM: Glycine max
<220> FEATURE:
<221> NAME/KEY: unsure
<222> LOCATION: (32)
<221> NAME/KEY: unsure
<222> LOCATION: (66)
<221> NAME/KEY: unsure
<222> LOCATION: (68)
<221> NAME/KEY: unsure
<222> LOCATION: (77)
<221> NAME/KEY: unsure
<222> LOCATION: (342)
<221> NAME/KEY: unsure
<222> LOCATION: (380)
<221> NAME/KEY: unsure
<222> LOCATION: (442)
<221> NAME/KEY: unsure
<222> LOCATION: (459)
<221> NAME/KEY: unsure
<222> LOCATION: (466)
<221> NAME/KEY: unsure
<222> LOCATION: (486)
<221> NAME/KEY: unsure
<222> LOCATION: (491)
<221> NAME/KEY: unsure
<222> LOCATION: (499)..(500)
<221> NAME/KEY: unsure
<222> LOCATION: (509)
<221> NAME/KEY: unsure
<222> LOCATION: (511)

<400> SEQUENCE: 13
ttgggattga gtgaagaaac agtggtcgtt cnctctgaaa tgggtttcgc tttggcatac      60
acagcntntg ggttgtngct caaacctaca atttcagtct ctgttattcg ctgctgcttc     120
attgagatca aaaccgtgtc tctctctctg caactctact tatcgaccca aacgcattct     180
ccagcgttct ccaattgttg gcgctcagtc tgaaaatgga gctctggtta cttcggagaa     240
gcccgacact aattacggaa gacaatactt ccccctcgct gctgttgtag gccaagattc     300
tataaaaact gctcttttac ttggtgcaat tgaccccggg gntggaggaa ttgccatatc     360
aggaaagcga ggaatgccan aactgtaatg gcacgtggat tgatgaatac tgctcctatt     420
gagggagagg ttcattgcaa tnggatcaac tgccagaang gggaantgtc tacagatgct     480
gatatntctc nggaattann ctcgatacna n                                   511

<210> SEQ ID NO 14
<211> LENGTH: 109
<212> TYPE: PRT
<213> ORGANISM: Glycine max
<220> FEATURE:
<221> NAME/KEY: UNSURE
<222> LOCATION: (7)..(8)
<221> NAME/KEY: UNSURE
<222> LOCATION: (11)
<221> NAME/KEY: UNSURE
<222> LOCATION: (99)
```

<400> SEQUENCE: 14

Ser Leu Trp His Thr Gln Xaa Xaa Gly Cys Xaa Ser Asn Leu Gln Phe
 1               5                  10                  15

Gln Ser Leu Leu Phe Ala Ala Ala Ser Leu Arg Ser Lys Pro Cys Leu
            20                  25                  30

Ser Leu Cys Asn Ser Thr Tyr Arg Pro Lys Arg Ile Leu Gln Arg Ser
        35                  40                  45

Pro Ile Val Gly Ala Gln Ser Glu Asn Gly Ala Leu Val Thr Ser Glu
    50                  55                  60

Lys Pro Asp Thr Asn Tyr Gly Arg Gln Tyr Phe Pro Leu Ala Ala Val
 65                 70                  75                  80

Val Gly Gln Asp Ser Ile Lys Thr Ala Leu Leu Gly Ala Ile Asp
                85                  90                  95

Pro Gly Xaa Gly Gly Ile Ala Ile Ser Gly Lys Arg Gly
            100                 105

<210> SEQ ID NO 15
<211> LENGTH: 438
<212> TYPE: DNA
<213> ORGANISM: Triticum aestivum
<220> FEATURE:
<221> NAME/KEY: unsure
<222> LOCATION: (401)

<400> SEQUENCE: 15
ggcagcatgg ctctgaaccg catgcagaat gccaaggtg cagcattgaa gttgcttgca      60
gaaagttaca caagcagaga tcaggttgca attattccct tccgtggaga ctatgctgag    120
gttctgcttc caccatcaag atccattgca atggctcgca acgtcttga aaagctacca    180
tgcggtggcg gttctccttt agctcatggc ctgagtacag ctgtcagagt gggattgaac    240
gctgaaaaga gtggcgacgt tgggcgtatc atggaattcg gttggccaaa tcacccggat    300
ggaaagaagc taaatggtta tcaactggaa gaaatccaaa tgacccagaa gctgcagctg    360
cttcagacgc accaagacca tctactcaag aattgaaggg ngagatactt gatgtgtctg    420
cagggagatc agggcagg                                                  438

<210> SEQ ID NO 16
<211> LENGTH: 91
<212> TYPE: PRT
<213> ORGANISM: Triticum aestivum

<400> SEQUENCE: 16

Gly Ser Met Ala Leu Asn Arg Met Gln Asn Ala Lys Gly Ala Ala Leu
 1               5                  10                  15

Lys Leu Leu Ala Glu Ser Tyr Thr Ser Arg Asp Gln Val Ala Ile Ile
            20                  25                  30

Pro Phe Arg Gly Asp Tyr Ala Glu Val Leu Leu Pro Pro Ser Arg Ser
        35                  40                  45

Ile Ala Met Ala Arg Lys Arg Leu Glu Lys Leu Pro Cys Gly Gly Gly
    50                  55                  60

Ser Pro Leu Ala His Gly Leu Ser Thr Ala Val Arg Val Gly Leu Asn
 65                 70                  75                  80

Ala Glu Lys Ser Gly Asp Val Gly Arg Ile Met
                85                  90

<210> SEQ ID NO 17

<211> LENGTH: 912
<212> TYPE: DNA
<213> ORGANISM: Triticum aestivum

<400> SEQUENCE: 17

```
gcacgagggc agcatggctc tgaaccgcat gcagaatgcc aaaggtgcag cattgaagtt      60
gcttgcagaa agttacacaa gcagagatca ggttgcaatt attcccttcc gtggagacta     120
tgctgaggtt ctgcttccac catcaagatc cattgcaatg gctcgcaaac gtcttgaaaa     180
gctaccatgc ggtggcggtt ctcctttagc tcatggcctg agtacagctg tcagagtggg     240
attgaacgct gaaaagagtg gcgacgttgg gcgtatcatg atcgttgcaa tcaccgatgg     300
aagagctaat gtatcactga gaaatccaa tgacccagaa gctgcagctg cttcagacgc      360
accaagacca tctactcaag aattgaagga tgagatactt gatgtgtctg caaaatatt      420
caaagcagga atgtcgcttc tcgtcatcga taccgagaac aagtttgtat ctacgggatt     480
cgccaaggaa atcgcaaggg ttgcccaagg gaaatactac tacctgccaa acgcttcgga     540
cgccgtgatt tcggccgcca ccaagaccgc gctggcggac ttgaagagct agagagcgat     600
ctcggagcgt cgatcagcac ccgcccaact attgtttgta ccgtctgatg ataaaagttg     660
tttcgtgcag taatttgtgc agctgtcctt agttctttct gtaacttttt tgggacgtgc     720
gtttcagctc ttatgaccca attttggtgt aggttttctt ttcttctttc tttctctttt     780
accagcacca gcagggctaa agtccgagca taacttcgtg taaatgtcgg aattctccca     840
ctgcctctct gataattggc cttgtaaatc tactgctgtt aattttcgag gcagaaaaaa     900
aaaaaaaaaa aa                                                         912
```

<210> SEQ ID NO 18
<211> LENGTH: 196
<212> TYPE: PRT
<213> ORGANISM: Triticum aestivum

<400> SEQUENCE: 18

```
His Glu Gly Ser Met Ala Leu Asn Arg Met Gln Asn Ala Lys Gly Ala
  1               5                  10                  15

Ala Leu Lys Leu Leu Ala Glu Ser Tyr Thr Ser Arg Asp Gln Val Ala
                 20                  25                  30

Ile Ile Pro Phe Arg Gly Asp Tyr Ala Glu Val Leu Leu Pro Pro Ser
             35                  40                  45

Arg Ser Ile Ala Met Ala Arg Lys Arg Leu Glu Lys Leu Pro Cys Gly
         50                  55                  60

Gly Gly Ser Pro Leu Ala His Gly Leu Ser Thr Ala Val Arg Val Gly
 65                  70                  75                  80

Leu Asn Ala Glu Lys Ser Gly Asp Val Gly Arg Ile Met Ile Val Ala
                 85                  90                  95

Ile Thr Asp Gly Arg Ala Asn Val Ser Leu Lys Lys Ser Asn Asp Pro
            100                 105                 110

Glu Ala Ala Ala Ser Asp Ala Pro Arg Pro Ser Thr Gln Glu Leu
            115                 120                 125

Lys Asp Glu Ile Leu Asp Val Ser Ala Lys Ile Phe Lys Ala Gly Met
        130                 135                 140

Ser Leu Leu Val Ile Asp Thr Glu Asn Lys Phe Val Ser Thr Gly Phe
145                 150                 155                 160

Ala Lys Glu Ile Ala Arg Val Ala Gln Gly Lys Tyr Tyr Tyr Leu Pro
                165                 170                 175
```

Asn Ala Ser Asp Ala Val Ile Ser Ala Ala Thr Lys Thr Ala Leu Ala
            180                 185                 190

Asp Leu Lys Ser
            195

<210> SEQ ID NO 19
<211> LENGTH: 583
<212> TYPE: DNA
<213> ORGANISM: Zea mays
<220> FEATURE:
<221> NAME/KEY: unsure
<222> LOCATION: (397)
<221> NAME/KEY: unsure
<222> LOCATION: (442)
<221> NAME/KEY: unsure
<222> LOCATION: (464)
<221> NAME/KEY: unsure
<222> LOCATION: (470)
<221> NAME/KEY: unsure
<222> LOCATION: (480)
<221> NAME/KEY: unsure
<222> LOCATION: (503)
<221> NAME/KEY: unsure
<222> LOCATION: (514)..(515)
<221> NAME/KEY: unsure
<222> LOCATION: (523)
<221> NAME/KEY: unsure
<222> LOCATION: (540)
<221> NAME/KEY: unsure
<222> LOCATION: (574)
<221> NAME/KEY: unsure
<222> LOCATION: (583)

<400> SEQUENCE: 19
gtcgtccgta accgccgccg tgcagcagct caacgccgac ccgcgccgcg ccgccgcgtt      60
cgaggtcgtg ggctacctcg tcgaggagct ccgcgacgag gacacctacg ccaccttctg     120
cgccgacctc gccgacgcca acgtcttcat cggctcccte atcttcgtcg aggagctggc     180
cctcaaggtc aaggccgccg tcgagaagga gcgcgaccgc atggacgccg tcctcgtctt     240
cccctcaatg cccgaggtca tgcgcctcaa caagctcggc tccttcagca tgtcgcaagc     300
tggggcagtc caaagagccc cttcttccag ctcttcaagc gcaacaaggg caactccaag     360
caactttcgc cgacaagaat gctcaaagct cgtccgnaag gctgccaaag gtgctcaaag     420
taacttggcc tctgacaaag gngcaaggac gccccggggt ctanattctn aagcttcaan     480
tctgggtccg tgggtccccc ggncaaactc caanngatttc tcnaagatga ttgccgggtn     540
ctaaatggct ggcctcaaag ggggccggat caantacgaa gan                      583

<210> SEQ ID NO 20
<211> LENGTH: 118
<212> TYPE: PRT
<213> ORGANISM: Zea mays

<400> SEQUENCE: 20

Ser Ser Val Thr Ala Ala Val Gln Gln Leu Asn Ala Asp Arg Arg Ala
  1               5                  10                  15

Ala Ala Phe Glu Val Val Gly Tyr Leu Val Glu Glu Leu Arg Asp Glu
                 20                  25                  30

Asp Thr Tyr Ala Thr Phe Cys Ala Asp Leu Ala Asp Ala Asn Val Phe
             35                  40                  45

Ile Gly Ser Leu Ile Phe Val Glu Glu Leu Ala Leu Lys Val Lys Ala
         50                  55                  60

Ala Val Glu Lys Glu Arg Asp Arg Met Asp Ala Val Leu Val Phe Pro
 65                  70                  75                  80

```
Ser Met Pro Glu Val Met Arg Leu Asn Lys Leu Gly Ser Phe Ser Met
                85                  90                  95

Ser Gln Ala Gly Gly Ser Pro Lys Ser Pro Phe Phe Gln Leu Phe Lys
            100                 105                 110

Arg Asn Lys Gly Asn Ser
        115

<210> SEQ ID NO 21
<211> LENGTH: 782
<212> TYPE: DNA
<213> ORGANISM: Zea mays

<400> SEQUENCE: 21
gcacgaggtc gtccgtaacc gccgccgtgc agcagctcaa cgccgacccg cgccgcgccg      60
ccgcgttcga ggtcgtgggc tacctcgtcg aggagctccg cgacgaggac acctacgcca     120
ccttctgcgc cgacctcgcc gacgccaacg tcttcatcgg ctccctcatc ttcgtcgagg     180
agctggccct caaggtcaag gccgccgtcg agaaggagcg cgaccgcatg gacgccgtcc     240
tcgtcttccc ctcaatgccc gaggtcatgc gcctcaacaa gctcggctcc ttcagcatgt     300
cgcagctggg gcagtccaag agccccttct ccagctctt caagcgcaac aaggccaact     360
ccagcaactt cgccgacagc atgctcaagc tcgtccgcac gctgcccaag gtgctcaagt     420
acctgccctc tgacaaggcg caggacgccc ggctctacat cctcagcctc cagttctggc     480
tcggtggctc gccggacaac ctccagaact tcctcaagat gatcgccggc tcctacgtgc     540
ctgccctcaa gggcgccggc atcaagtacg acgacccgt tctctacctc gactccggca     600
tctggcaccc gctggcgccc accatgtacg aggacgtcaa ggagtacctc aactggtacg     660
gcacgcgccg ggacgccaac gacaggctca aggaccccaa ggcgcccatc atcggcctcg     720
tcctgcagag gagccacatt gtcaccggcg acgacgggca ctacgtcgcc gtcatcatgg     780
ag                                                                   782

<210> SEQ ID NO 22
<211> LENGTH: 260
<212> TYPE: PRT
<213> ORGANISM: Zea mays

<400> SEQUENCE: 22

Thr Arg Ser Ser Val Thr Ala Ala Val Gln Gln Leu Asn Ala Asp Pro
  1               5                  10                  15

Arg Arg Ala Ala Ala Phe Glu Val Val Gly Tyr Leu Val Glu Glu Leu
            20                  25                  30

Arg Asp Glu Asp Thr Tyr Ala Thr Phe Cys Ala Asp Leu Ala Asp Ala
        35                  40                  45

Asn Val Phe Ile Gly Ser Leu Ile Phe Val Glu Leu Ala Leu Lys
     50                  55                  60

Val Lys Ala Ala Val Glu Lys Glu Arg Asp Arg Met Asp Ala Val Leu
 65                  70                  75                  80

Val Phe Pro Ser Met Pro Glu Val Met Arg Leu Asn Lys Leu Gly Ser
                 85                  90                  95

Phe Ser Met Ser Gln Leu Gly Gln Ser Lys Ser Pro Phe Phe Gln Leu
            100                 105                 110

Phe Lys Arg Asn Lys Ala Asn Ser Ser Asn Phe Ala Asp Ser Met Leu
        115                 120                 125

Lys Leu Val Arg Thr Leu Pro Lys Val Leu Lys Tyr Leu Pro Ser Asp
```

```
               130                135                140
Lys Ala Gln Asp Ala Arg Leu Tyr Ile Leu Ser Leu Gln Phe Trp Leu
145                 150                 155                 160

Gly Gly Ser Pro Asp Asn Leu Gln Asn Phe Leu Lys Met Ile Ala Gly
                165                 170                 175

Ser Tyr Val Pro Ala Leu Lys Gly Ala Gly Ile Lys Tyr Asp Asp Pro
                180                 185                 190

Val Leu Tyr Leu Asp Ser Gly Ile Trp His Pro Leu Ala Pro Thr Met
            195                 200                 205

Tyr Glu Asp Val Lys Glu Tyr Leu Asn Trp Tyr Gly Thr Arg Arg Asp
        210                 215                 220

Ala Asn Asp Arg Leu Lys Asp Pro Lys Ala Pro Ile Ile Gly Leu Val
225                 230                 235                 240

Leu Gln Arg Ser His Ile Val Thr Gly Asp Asp Gly His Tyr Val Ala
                245                 250                 255

Val Ile Met Glu
            260
```

<210> SEQ ID NO 23
<211> LENGTH: 507
<212> TYPE: DNA
<213> ORGANISM: Zea mays
<220> FEATURE:
<221> NAME/KEY: unsure
<222> LOCATION: (79)
<221> NAME/KEY: unsure
<222> LOCATION: (498)

<400> SEQUENCE: 23

```
tattgcccac gaccaagttc gtcagagcgg acagagagaa gatgagggtt ctgtttgggt     60
tcttggggga gtgcctgang ctcgtcgtgc aagacaacga gctgggaagc ttgaagcttg    120
ccctcgaggg aagctacgtc gagcctggac ctggcggcga cccgatccgt aacccgaagt    180
gctcccgaca ggaagaacat ccacgctctc gatccgcagg ccatcccaac cacggctgcc    240
ttgaagagcg ccaagatcgt cgtggaccgt ctcctggaga ggcagaaggc tgacaatggc    300
ggcaagtacc ctgagacggt cgcacttgtc ctgtggggca ccgacaacat caagacctat    360
ggtgagtcac tagcccaggt gctgtggatg attggagttc ggccagttgc cgacaccttc    420
ggccgtgtca accgtgtgga gcctgtcagc cttgaggagc ttggacgccc aaggatcgat    480
gtcgtcgtca attgctcngg gtgtttt                                        507
```

<210> SEQ ID NO 24
<211> LENGTH: 108
<212> TYPE: PRT
<213> ORGANISM: Zea mays

<400> SEQUENCE: 24

```
Pro Asp Arg Lys Asn Ile His Ala Leu Asp Pro Gln Ala Ile Pro Thr
1               5                   10                  15

Thr Ala Ala Leu Lys Ser Ala Lys Ile Val Val Asp Arg Leu Leu Glu
            20                  25                  30

Arg Gln Lys Ala Asp Asn Gly Gly Lys Tyr Pro Glu Thr Val Ala Leu
        35                  40                  45

Val Leu Trp Gly Thr Asp Asn Ile Lys Thr Tyr Gly Glu Ser Leu Ala
    50                  55                  60

Gln Val Leu Trp Met Ile Gly Val Arg Pro Val Ala Asp Thr Phe Gly
65                  70                  75                  80
```

```
Arg Val Asn Arg Val Glu Pro Val Ser Leu Glu Glu Leu Gly Arg Pro
            85                  90                  95

Arg Ile Asp Val Val Asn Cys Ser Gly Cys Phe
        100                 105
```

```
<210> SEQ ID NO 25
<211> LENGTH: 351
<212> TYPE: DNA
<213> ORGANISM: Zea mays
<220> FEATURE:
<221> NAME/KEY: unsure
<222> LOCATION: (202)
<221> NAME/KEY: unsure
<222> LOCATION: (257)
<221> NAME/KEY: unsure
<222> LOCATION: (267)
<221> NAME/KEY: unsure
<222> LOCATION: (284)
<221> NAME/KEY: unsure
<222> LOCATION: (288)
<221> NAME/KEY: unsure
<222> LOCATION: (299)
<221> NAME/KEY: unsure
<222> LOCATION: (301)
<221> NAME/KEY: unsure
<222> LOCATION: (333)

<400> SEQUENCE: 25
tattgcacac agcgctacct ggtcgacccg attaccggca agacgttcgt gaacgccgtg      60
gtgtctctca ccgggttcgc gctcgtcggg gggccggcga ggcaggacca tcccaaggcc     120
attgccgcgc tgcagaagct cgacgtgccg tacattgtcg cgctcccgct cgtgttccag     180
accacggagg agtggctcaa cnagcacctt ggggcttcac ccaattcagg tggcgctgca     240
ggtcgcgctg ccggagntcg acggtgngat ggagcccatt cgtngttncg ccggcggana     300 ncccaagga caggggaagt cccaatgcat tgnacaagag acttggagca g               351
```

```
<210> SEQ ID NO 26
<211> LENGTH: 103
<212> TYPE: PRT
<213> ORGANISM: Zea mays
<220> FEATURE:
<221> NAME/KEY: UNSURE
<222> LOCATION: (87)
<221> NAME/KEY: UNSURE
<222> LOCATION: (90)
<221> NAME/KEY: UNSURE
<222> LOCATION: (96)..(97)
<221> NAME/KEY: UNSURE
<222> LOCATION: (101)

<400> SEQUENCE: 26

Gln Arg Tyr Leu Val Asp Pro Ile Thr Gly Lys Thr Phe Val Asn Ala
 1               5                  10                  15

Val Val Ser Leu Thr Gly Phe Ala Leu Val Gly Gly Pro Ala Arg Gln
            20                  25                  30

Asp His Pro Lys Ala Ile Ala Ala Leu Gln Lys Leu Asp Val Pro Tyr
        35                  40                  45

Ile Val Ala Leu Pro Leu Val Phe Gln Thr Thr Glu Glu Trp Leu Asn
    50                  55                  60

Glu Trp Leu Asn Ser Thr Leu Gly Leu His Pro Ile Gln Val Ala Leu
65                  70                  75                  80

Gln Val Ala Leu Pro Glu Xaa Asp Gly Xaa Met Glu Pro Ile Arg Xaa
                85                  90                  95
```

Xaa Ala Gly Gly Xaa Pro Gln
          100

<210> SEQ ID NO 27
<211> LENGTH: 439
<212> TYPE: DNA
<213> ORGANISM: Zea mays

<400> SEQUENCE: 27
ggcacgccca ggagcaggcg gaggagctcg gcgtgtcgct aagggaggcg gcgacaaggg    60
tgttctcgaa cgcatcaggc tcctactcgt ccaacgtgaa cctggcggtg gagaacgcgt   120
catggaccga cgagaagcag ctccaggaca tgtacctgag ccgcaagtcc ttcgcgttcg   180
acagcgacgc ccctggggca ggcatgaagg agaagcgcaa ggcgttcgag ctcgccctgg   240
cgacggcgga cgccacgttc cagaacctcg actcgtcgga gatctcgctg acggacgtga   300 gcccactactt tcgacttcgg acccgaccaa gctcgtgcag gggcttgcgc aaggacgggc   360
gggcgccgtc cttcgtacat aagccgacac caacacggcg aacgcccaag tgaagacgct   420
gtcggagaag gtgcgcctt                                                 439

<210> SEQ ID NO 28
<211> LENGTH: 136
<212> TYPE: PRT
<213> ORGANISM: Zea mays

<400> SEQUENCE: 28

His Ala Gln Glu Gln Ala Glu Glu Leu Gly Val Ser Leu Arg Glu Ala
  1               5                  10                  15

Ala Thr Arg Val Phe Ser Asn Ala Ser Gly Ser Tyr Ser Ser Asn Val
                 20                  25                  30

Asn Leu Ala Val Glu Asn Ala Ser Trp Thr Asp Glu Lys Gln Leu Gln
             35                  40                  45

Asp Met Tyr Leu Ser Arg Lys Ser Phe Ala Phe Asp Ser Asp Ala Pro
         50                  55                  60

Gly Ala Gly Met Lys Glu Lys Arg Lys Ala Phe Glu Leu Ala Leu Ala
 65                  70                  75                  80

Thr Ala Asp Ala Thr Phe Gln Asn Leu Asp Ser Ser Glu Ile Ser Leu
                 85                  90                  95

Thr Asp Val Ser His Tyr Phe Arg Leu Arg Thr Arg Pro Ser Ser Cys
                100                 105                 110

Arg Gly Leu Arg Lys Asp Gly Arg Ala Pro Ser Phe Val His Lys Pro
            115                 120                 125

Thr Pro Thr Arg Arg Thr Pro Lys
        130                 135

<210> SEQ ID NO 29
<211> LENGTH: 378
<212> TYPE: DNA
<213> ORGANISM: Zea mays
<220> FEATURE:
<221> NAME/KEY: unsure
<222> LOCATION: (27)
<221> NAME/KEY: unsure
<222> LOCATION: (70)
<221> NAME/KEY: unsure
<222> LOCATION: (109)
<221> NAME/KEY: unsure
<222> LOCATION: (114)
<221> NAME/KEY: unsure
<222> LOCATION: (163)
<221> NAME/KEY: unsure
<222> LOCATION: (261)
<221> NAME/KEY: unsure
<222> LOCATION: (266)
<221> NAME/KEY: unsure
<222> LOCATION: (292)
<221> NAME/KEY: unsure
<222> LOCATION: (305)
<221> NAME/KEY: unsure
<222> LOCATION: (342)
<221> NAME/KEY: unsure
<222> LOCATION: (356)

<400> SEQUENCE: 29

```
gaccgccccg aggacggcat aacctcnctg cccggcatac ttgccgccac agtgggcagg     60
gacattgaan atgtgtacag gggaagtgac aagggcatac tggctgacnt cgancttctg    120
aggcagatca ctgaggcttc gcgcggcgcc atcaccgcct tcnttgagaa gaccacaaac    180
agcaaagggc aggtcgtcaa tgttaccaac aacctcagca agatacttgg tttcggtctg    240
tcggaaccat gggtgcaata nctgtncacg accaagttcg tcagagcggg anagagagaa    300
gatgnagggt tctgtttggg ttcttagggg agtgcctgaa gntcgtcgtg ccaaanaacg    360
agctggggaa agcttgaa                                                  378
```

<210> SEQ ID NO 30
<211> LENGTH: 108
<212> TYPE: PRT
<213> ORGANISM: Zea mays
<220> FEATURE:
<221> NAME/KEY: UNSURE
<222> LOCATION: (24)
<221> NAME/KEY: UNSURE
<222> LOCATION: (37)..(38)
<221> NAME/KEY: UNSURE
<222> LOCATION: (55)
<221> NAME/KEY: UNSURE
<222> LOCATION: (87)
<221> NAME/KEY: UNSURE
<222> LOCATION: (89)
<221> NAME/KEY: UNSURE
<222> LOCATION: (98)
<221> NAME/KEY: UNSURE
<222> LOCATION: (102)

<400> SEQUENCE: 30

```
Asp Arg Pro Glu Asp Gly Ile Thr Ser Leu Pro Gly Ile Leu Ala Ala
 1               5                  10                  15

Thr Val Gly Arg Asp Ile Glu Xaa Val Tyr Arg Gly Ser Asp Lys Gly
                20                  25                  30

Ile Leu Ala Asp Xaa Xaa Leu Leu Arg Gln Ile Thr Glu Ala Ser Arg
            35                  40                  45

Gly Ala Ile Thr Ala Phe Xaa Glu Lys Thr Thr Asn Ser Lys Gly Gln
    50                  55                  60

Val Val Asn Val Thr Asn Asn Leu Ser Lys Ile Leu Gly Phe Gly Leu
65                  70                  75                  80

Ser Glu Pro Trp Val Gln Xaa Leu Xaa Thr Thr Lys Phe Val Arg Ala
                85                  90                  95

Gly Xaa Arg Glu Asp Xaa Gly Phe Cys Leu Gly Ser
            100                 105
```

<210> SEQ ID NO 31
<211> LENGTH: 495
<212> TYPE: DNA
<213> ORGANISM: Zea mays
<220> FEATURE:
<221> NAME/KEY: unsure
<222> LOCATION: (9)
<221> NAME/KEY: unsure
<222> LOCATION: (269)
<221> NAME/KEY: unsure
<222> LOCATION: (368)
<221> NAME/KEY: unsure
<222> LOCATION: (381)
<221> NAME/KEY: unsure
<222> LOCATION: (404)
<221> NAME/KEY: unsure
<222> LOCATION: (451)
<221> NAME/KEY: unsure
<222> LOCATION: (457)
<221> NAME/KEY: unsure
<222> LOCATION: (460)
<221> NAME/KEY: unsure
<222> LOCATION: (466)

<400> SEQUENCE: 31

```
ggtacgaang tgatcccatg cggcttctct tctcaaagtc tgccagccct caccatggat      60
ttgcagcata ctacaccttt gtcgagaaga tcttccaggc cgatgctgtt ctgcactttg     120
gaacacacgg gtccctcgag ttcatgcctg gcaagcaggt tgggatgagt gacgcctgct     180
tccctgacag cctcattggc aacatcccca acatctacta ctatgctgca aacaacccat     240
cagaagccac ggtgggccaa gcgccgganc tacgcgaaca ccatcagcta cctgaaccca     300
ccgggcgaaa aacgccgggc tctacaaggg gctcaagcag ctgttcagaa ctcatctctt     360
cctaccantc tcttcaagga naccggggtt gtcctcaaat tgtnaactcc atcgtcagca     420
ctgcaaacaa tgcaacctcc aaaagatttt ncgctgnccn aagaagggga agaatcccac     480
caaagaactt aactt                                                      495
```

<210> SEQ ID NO 32
<211> LENGTH: 164
<212> TYPE: PRT
<213> ORGANISM: Zea mays
<220> FEATURE:
<221> NAME/KEY: UNSURE
<222> LOCATION: (3)
<221> NAME/KEY: UNSURE
<222> LOCATION: (89)
<221> NAME/KEY: UNSURE
<222> LOCATION: (122)
<221> NAME/KEY: UNSURE
<222> LOCATION: (127)
<221> NAME/KEY: UNSURE
<222> LOCATION: (150)
<221> NAME/KEY: UNSURE
<222> LOCATION: (152)..(153)
<221> NAME/KEY: UNSURE
<222> LOCATION: (155)

<400> SEQUENCE: 32

```
Tyr Glu Xaa Asp Pro Met Arg Leu Leu Phe Ser Lys Ser Ala Ser Pro
 1               5                  10                  15

His His Gly Phe Ala Ala Tyr Tyr Thr Phe Val Glu Lys Ile Phe Gln
             20                  25                  30

Ala Asp Ala Val Leu His Phe Gly Thr His Gly Ser Leu Glu Phe Met
         35                  40                  45

Pro Gly Lys Gln Val Gly Met Ser Asp Ala Cys Phe Pro Asp Ser Leu
     50                  55                  60

Ile Gly Asn Ile Pro Asn Ile Tyr Tyr Ala Ala Asn Asn Pro Ser
 65                  70                  75                  80

Glu Ala Thr Val Gly Gln Ala Pro Xaa Leu Arg Glu His His Gln Leu
             85                  90                  95
```

```
Pro Glu Pro Thr Gly Arg Lys Thr Pro Gly Ser Thr Arg Gly Ser Ser
            100                 105                 110

Ser Cys Ser Glu Leu Ile Ser Ser Tyr Xaa Ser Leu Gln Gly Xaa Arg
        115                 120                 125

Gly Cys Pro Gln Ile Val Asn Ser Ile Val Ser Thr Ala Asn Asn Ala
    130                 135                 140

Thr Ser Lys Arg Phe Xaa Ala Xaa Xaa Arg Xaa Gly Arg Ile Pro Pro
145                 150                 155                 160

Lys Asn Leu Thr

<210> SEQ ID NO 33
<211> LENGTH: 652
<212> TYPE: DNA
<213> ORGANISM: Oryza sativa
<220> FEATURE:
<221> NAME/KEY: unsure
<222> LOCATION: (347)
<221> NAME/KEY: unsure
<222> LOCATION: (392)
<221> NAME/KEY: unsure
<222> LOCATION: (400)
<221> NAME/KEY: unsure
<222> LOCATION: (419)
<221> NAME/KEY: unsure
<222> LOCATION: (421)..(422)
<221> NAME/KEY: unsure
<222> LOCATION: (474)
<221> NAME/KEY: unsure
<222> LOCATION: (502)
<221> NAME/KEY: unsure
<222> LOCATION: (504)
<221> NAME/KEY: unsure
<222> LOCATION: (513)
<221> NAME/KEY: unsure
<222> LOCATION: (534)
<221> NAME/KEY: unsure
<222> LOCATION: (589)
<221> NAME/KEY: unsure
<222> LOCATION: (595)
<221> NAME/KEY: unsure
<222> LOCATION: (597)
<221> NAME/KEY: unsure
<222> LOCATION: (605)
<221> NAME/KEY: unsure
<222> LOCATION: (607)
<221> NAME/KEY: unsure
<222> LOCATION: (623)
<221> NAME/KEY: unsure
<222> LOCATION: (638)
<221> NAME/KEY: unsure
<222> LOCATION: (644)
<221> NAME/KEY: unsure
<222> LOCATION: (648)

<400> SEQUENCE: 33
atcactcctc aagggcgccg acatcaagta cgacgacccc gtcctcttcc tcgacgctgg      60
tatctggcac ccgctggcgc ccaccatgta cgacgacgtc aaggagtacc tcaactggta     120
cggcacccgc cgcgacacca acgacaagct caaggacccc aacgcgccgg tgatcggcct     180
cgttttgcag aggagccaca ttgtcaccgg agacgacggt cactacgtcg ccgtgatcat     240
ggagctggag gccaagggtg ccaaggtcat accgatcttc gccggcgggc tgggacttct     300
cggggaccca cgcagcgggt acctcgtcaa cccgatcacc gggaaanctt cgtgaacgcg     360
gtgggtgtcg ctcaccgggt tcgcgctcgt cngagggcan cgagcaagac atcccaagng     420
nngccgcgct gcaaaactcg actgccgtca tcgtggatgc cctcgtgtca aacnaagaag     480
atggtgaaca caatgggctg ancnaataag tgngctcaag tgcctcccgg actnacgtgg     540
```

```
aaggaccatg gttcccggcg taccaaaaag gaataaatct tgaaaaggng gcacntncaa    600
acatnantgg aaactaaagg aanagggaa aacgaacncg tttnctcnaa aa             652
```

<210> SEQ ID NO 34
<211> LENGTH: 114
<212> TYPE: PRT
<213> ORGANISM: Oryza sativa
<220> FEATURE:
<221> NAME/KEY: UNSURE
<222> LOCATION: (113)

<400> SEQUENCE: 34

```
Leu Lys Gly Ala Asp Ile Lys Tyr Asp Asp Pro Val Leu Phe Leu Asp
  1               5                  10                  15

Ala Gly Ile Trp His Pro Leu Ala Pro Thr Met Tyr Asp Asp Val Lys
             20                  25                  30

Glu Tyr Leu Asn Trp Tyr Gly Thr Arg Arg Asp Thr Asn Asp Lys Leu
         35                  40                  45

Lys Asp Pro Asn Ala Pro Val Ile Gly Leu Val Leu Gln Arg Ser His
     50                  55                  60

Ile Val Thr Gly Asp Asp Gly His Tyr Val Ala Val Ile Met Glu Leu
 65                  70                  75                  80

Glu Ala Lys Gly Ala Lys Val Ile Pro Ile Phe Ala Gly Gly Leu Gly
                 85                  90                  95

Leu Leu Gly Pro Arg Ser Gly Tyr Leu Val Asn Pro Ile Thr Gly Lys
            100                 105                 110

Xaa Ser
```

<210> SEQ ID NO 35
<211> LENGTH: 3521
<212> TYPE: DNA
<213> ORGANISM: Oryza sativa

<400> SEQUENCE: 35

```
gcacgagatc actcctcaag ggcgccgaca tcaagtacga cgaccccgtc ctcttcctcg    60
acgctggtat ctggcacccg ctggcgccca ccatgtacga cgacgtcaag gagtacctca   120
actggtacgg cacccgccgc gacaccaacg acaagctcaa ggaccccaac gcgccggtga   180
tcggcctcgt tttgcagagg agccacattg tcaccggaga cgacggtcac tacgtcgccg   240
tgatcatgga gctggaggcc aagggtgcca aggtcatacc gatcttcgcc ggcgggctgg   300
acttctcggg acccacgcag cggtacctcg tcgacccgat caccggaaag ccgttcgtga   360
acgcggtggt gtcgctcacc gggttcgcgc tcgtcggagg gccagcgagg caggaccatc   420
ccaaggcgat cgccgcgctg cagaagctcg acgtgccgta catcgtggca ctgccgctcg   480
tgttccagac gacagaggag tggctgaaca gcacattggg cctgcacccg attcaggtgg   540
cgctgcaggt tgcgctcccg gagcttgacg gtggcatgga gcccattgtg ttcgccggcc   600
gtgaccccag aacaggaag tcacatgcgt tgcacaagag ggtggagcag ctctgcacta   660
gagcaatcag atgggcagag ctgaagagga aaactaagga ggagaagaaa ctggcaatca   720
ctgttttcag cttccaccca gacaaaggca atgttggcac agcagcatac ctgaatgttt   780
tcaactccat ctactccgtc ctccaagatc tgaagaagga tggctacaat gttgagggtc   840
ttccagacac agctgaggcc ctcatcgagg aggttattca tgataaggag gcccaattca   900
atagccccaa cctcaatgtt gcttaccgca tgaacgtgcg ggagtaccag tcactcactt   960
cctatgcctc cttgctggag gagaactggg gcaagccacc tgggaacctt aattctgatg  1020
```

-continued

```
gtgaaaacct ccttgtctat gggaaacagt acggcaatgt attcattgga gttcagccca    1080
cttttggcta tgaaggagat ccgatgcggc ttctgttctc aaaatctgct agccctcacc    1140
atggctttgc agcatactac acctttgttg agaagatctt ccaggctgat gctgttcttc    1200
actttggtac ccatgggtct cttgagttca tgccagggaa gcaggttggg atgagtgatg    1260
catgctatcc tgacagtctc attggcaaca tccccaatat ctactactat gcagcaaaca    1320
atccatcaga agcaactgtt gccaagcgca gaagctatgc aaacaccata agctacctga    1380
caccaccagc tgaaaatgct ggtctctaca aggggctcaa gcagctttca ggagctcatc    1440
tcttcttaac caatctctca aggacacagg acgtggtccg cagattgtga gctcaatcat    1500
tagcactgca aacagtgta atcttgacaa ggatgttccc ttgcctgagg aaggtgtgga    1560
gcttccacca aatgagcgtg accttattgt tggaaggtg tatgccaaga tcatggaaat    1620
agaatcacgc ctcctaccat gcggtctgca tgtgataggt gagccaccaa gtgccatcga    1680
ggctgtggcc accttggtga acatagcttc ccttgatcgc ccagaggatg aaatatactc    1740
actgcctaac atacttgctc agacagtggg caggaacatt gaagatgtgt acagaggaag    1800
tgacaaggga atactggcgg atgttgaact gttgaggcag ataacagaag cttcacgtgg    1860
tgccatcact accttttgttg agaggactac aaacaacaaa gggcaagttg ttgatgttac    1920
aaacaaactt agtaccatgc ttggttttgg tttatcagaa ccatgggtac aacacttgtc    1980
caagaccaag ttcatcagag cagacagaga gaaattgaga accttgttta ctttcttggg    2040
agaatgcttg aagctaattg tggcagataa tgagctggga agcttgaaac ttgccctcga    2100
gggaagctat gttgaacctg gccctggtgg tgatccaatc cgtaacccga aggttctccc    2160
gacagggaag aacatccatg ctcttgaccc tcaggcaatc ccaactacag ctgccttgaa    2220
gagcgccaaa attattgtag accgtctgct ggagcggcaa aaggttgaca atggtggcaa    2280
gtatcctgag acaattgcac ttgtcttgtg gggcaccgat aacatcaaga cctatggtga    2340
gtcattggcc caggtgctgt ggatgattgg tgtgcgcccg gttgctgaca cctttggccg    2400
tgtcaaccgt gtgaacctg tcagccttga ggagcttgga cgtcccagga ttgacgttgt    2460
tatcaactgc tcgggtgtct tcagagatct tttcatcaac cagatgaatc tactggaccg    2520
ggcagtgaag atggttgccg aactggatga gccagaagag atgaactacg tgcgtaagca    2580
tgcacaagag caggcacggg aacttggcgt tcattaaga gaggcggcaa caagggtgtt    2640
ctcaaatgca tcaggctctt actcatcgaa tgtgaacttg gcagtggaga atgcatcatg    2700
gactgatgag aagcagctcc aggacatgta cctgagtcgc aagtcttttg catttgattg    2760
tgatgctcca ggggcaggca tgcgagagca acgcaagaca tttgagcttg ctctagcaac    2820
agcagatgcc acattccaga acctagactc atcagagatt tcactaacag atgtgagcca    2880
ctactttgac tcagacccga caaagctggt gcaaggactg cgcaaggatg gcgggcacc    2940 ttcctcatac atagcagata caaccacagc aaatgcacag gtgaggacat tgtcagagac    3000
agtgcgcctt gatgcaagga caaagctact gaaccctaag tggtacgagg ggatgatgaa    3060
aagtggctac gagggagtta gagagattga gaagcggctg acaaatactg ttggatggag    3120
tgcaacatct ggacaggttg acaactgggt ttatgaggag gcaaatgcca catttattga    3180
agatgaggct atgaggaaga ggctcatgga caccaaccc aattcattca ggaagctagt    3240
tcagaccttc ctagaagcca gtggcagagg ctactgggag acatcagagg aaaacttgga    3300
aaagctcagg gagctctact ctgaggttga agacaagatt gaaggaattg accggtaaat    3360
```

-continued

```
ttatttgatc tatcagatcc tgcattcaac caaggaggag aaatccttct gtctcactga    3420
atctagagtt gagacttgta cactttgtat aatttataaa aagttgtaac atgacataca    3480
cgaggatacc gtgttttaac aaaaaaaaaa aaaaaaaaa a                         3521
```

<210> SEQ ID NO 36
<211> LENGTH: 1118
<212> TYPE: PRT
<213> ORGANISM: Oryza sativa

<400> SEQUENCE: 36

```
Thr Arg Ser Leu Leu Lys Gly Ala Asp Ile Lys Tyr Asp Asp Pro Val
  1               5                  10                  15

Leu Phe Leu Asp Ala Gly Ile Trp His Pro Leu Ala Pro Thr Met Tyr
             20                  25                  30

Asp Asp Val Lys Glu Tyr Leu Asn Trp Tyr Gly Thr Arg Arg Asp Thr
         35                  40                  45

Asn Asp Lys Leu Lys Asp Pro Asn Ala Pro Val Ile Gly Leu Val Leu
     50                  55                  60

Gln Arg Ser His Ile Val Thr Gly Asp Gly His Tyr Val Ala Val
 65                  70                  75                  80

Ile Met Glu Leu Glu Ala Lys Gly Ala Lys Val Ile Pro Ile Phe Ala
                 85                  90                  95

Gly Gly Leu Asp Phe Ser Gly Pro Thr Gln Arg Tyr Leu Val Asp Pro
            100                 105                 110

Ile Thr Gly Lys Pro Phe Val Asn Ala Val Val Ser Leu Thr Gly Phe
        115                 120                 125

Ala Leu Val Gly Gly Pro Ala Arg Gln Asp His Pro Lys Ala Ile Ala
    130                 135                 140

Ala Leu Gln Lys Leu Asp Val Pro Tyr Ile Val Ala Leu Pro Leu Val
145                 150                 155                 160

Phe Gln Thr Thr Glu Glu Trp Leu Asn Ser Thr Leu Gly Leu His Pro
                165                 170                 175

Ile Gln Val Ala Leu Gln Val Ala Leu Pro Glu Leu Asp Gly Gly Met
            180                 185                 190

Glu Pro Ile Val Phe Ala Gly Arg Asp Pro Arg Thr Gly Lys Ser His
        195                 200                 205

Ala Leu His Lys Arg Val Glu Gln Leu Cys Thr Arg Ala Ile Arg Trp
    210                 215                 220

Ala Glu Leu Lys Arg Lys Thr Lys Glu Glu Lys Leu Ala Ile Thr
225                 230                 235                 240

Val Phe Ser Phe Pro Pro Asp Lys Gly Asn Val Gly Thr Ala Ala Tyr
                245                 250                 255

Leu Asn Val Phe Asn Ser Ile Tyr Ser Val Leu Gln Asp Leu Lys Lys
            260                 265                 270

Asp Gly Tyr Asn Val Glu Gly Leu Pro Asp Thr Ala Glu Ala Leu Ile
        275                 280                 285

Glu Glu Val Ile His Asp Lys Glu Ala Gln Phe Asn Ser Pro Asn Leu
    290                 295                 300

Asn Val Ala Tyr Arg Met Asn Val Arg Glu Tyr Gln Ser Leu Thr Ser
305                 310                 315                 320

Tyr Ala Ser Leu Leu Glu Glu Asn Trp Gly Lys Pro Pro Gly Asn Leu
                325                 330                 335

Asn Ser Asp Gly Glu Asn Leu Leu Val Tyr Gly Lys Gln Tyr Gly Asn
            340                 345                 350
```

```
Val Phe Ile Gly Val Gln Pro Thr Phe Gly Tyr Glu Gly Asp Pro Met
            355                 360                 365
Arg Leu Leu Phe Ser Lys Ser Ala Ser Pro His His Gly Phe Ala Ala
        370                 375                 380
Tyr Tyr Thr Phe Val Glu Lys Ile Phe Gln Ala Asp Ala Val Leu His
385                 390                 395                 400
Phe Gly Thr His Gly Ser Leu Glu Phe Met Pro Gly Lys Gln Val Gly
                405                 410                 415
Met Ser Asp Ala Cys Tyr Pro Asp Ser Leu Ile Gly Asn Ile Pro Asn
            420                 425                 430
Ile Tyr Tyr Tyr Ala Ala Asn Asn Pro Ser Glu Ala Thr Val Ala Lys
        435                 440                 445
Arg Arg Ser Tyr Ala Asn Thr Ile Ser Tyr Leu Thr Pro Pro Ala Glu
    450                 455                 460
Asn Ala Gly Leu Tyr Lys Gly Leu Lys Gln Leu Ser Arg Ser Ser Ser
465                 470                 475                 480
Leu Leu Asn Gln Ser Leu Lys Asp Thr Gly Arg Gly Pro Gln Ile Val
                485                 490                 495
Ser Ser Ile Ile Ser Thr Ala Lys Gln Cys Asn Leu Asp Lys Asp Val
            500                 505                 510
Pro Leu Pro Glu Glu Gly Val Glu Leu Pro Pro Asn Glu Arg Asp Leu
        515                 520                 525
Ile Val Gly Lys Val Tyr Ala Lys Ile Met Glu Ile Glu Ser Arg Leu
    530                 535                 540
Leu Pro Cys Gly Leu His Val Ile Gly Glu Pro Pro Ser Ala Ile Glu
545                 550                 555                 560
Ala Val Ala Thr Leu Val Asn Ile Ala Ser Leu Asp Arg Pro Glu Asp
                565                 570                 575
Glu Ile Tyr Ser Leu Pro Asn Ile Leu Ala Gln Thr Val Gly Arg Asn
            580                 585                 590
Ile Glu Asp Val Tyr Arg Gly Ser Asp Lys Gly Ile Leu Ala Asp Val
        595                 600                 605
Glu Leu Leu Arg Gln Ile Thr Glu Ala Ser Arg Gly Ala Ile Thr Thr
    610                 615                 620
Phe Val Glu Arg Thr Thr Asn Asn Lys Gly Gln Val Val Asp Val Thr
625                 630                 635                 640
Asn Lys Leu Ser Thr Met Leu Gly Phe Gly Leu Ser Glu Pro Trp Val
                645                 650                 655
Gln His Leu Ser Lys Thr Lys Phe Ile Arg Ala Asp Arg Glu Lys Leu
            660                 665                 670
Arg Thr Leu Phe Thr Phe Leu Gly Glu Cys Leu Lys Leu Ile Val Ala
        675                 680                 685
Asp Asn Glu Leu Gly Ser Leu Lys Leu Ala Leu Glu Gly Ser Tyr Val
    690                 695                 700
Glu Pro Gly Pro Gly Gly Asp Pro Ile Arg Asn Pro Lys Val Leu Pro
705                 710                 715                 720
Thr Gly Lys Asn Ile His Ala Leu Asp Pro Gln Ala Ile Pro Thr Thr
                725                 730                 735
Ala Ala Leu Lys Ser Ala Lys Ile Ile Val Asp Arg Leu Leu Glu Arg
            740                 745                 750
Gln Lys Val Asp Asn Gly Gly Lys Tyr Pro Glu Thr Ile Ala Leu Val
        755                 760                 765
```

```
Leu Trp Gly Thr Asp Asn Ile Lys Thr Tyr Gly Glu Ser Leu Ala Gln
    770                 775                 780

Val Leu Trp Met Ile Gly Val Arg Pro Val Ala Asp Thr Phe Gly Arg
785                 790                 795                 800

Val Asn Arg Val Glu Pro Val Ser Leu Glu Glu Leu Gly Arg Pro Arg
                805                 810                 815

Ile Asp Val Val Ile Asn Cys Ser Gly Val Phe Arg Asp Leu Phe Ile
            820                 825                 830

Asn Gln Met Asn Leu Leu Asp Arg Ala Val Lys Met Val Ala Glu Leu
                835                 840                 845

Asp Glu Pro Glu Glu Met Asn Tyr Val Arg Lys His Ala Gln Glu Gln
            850                 855                 860

Ala Arg Glu Leu Gly Val Ser Leu Arg Glu Ala Ala Thr Arg Val Phe
865                 870                 875                 880

Ser Asn Ala Ser Gly Ser Tyr Ser Ser Asn Val Asn Leu Ala Val Glu
                885                 890                 895

Asn Ala Ser Trp Thr Asp Glu Lys Gln Leu Gln Asp Met Tyr Leu Ser
                900                 905                 910

Arg Lys Ser Phe Ala Phe Asp Cys Asp Ala Pro Gly Ala Gly Met Arg
            915                 920                 925

Glu Gln Arg Lys Thr Phe Glu Leu Ala Leu Ala Thr Ala Asp Ala Thr
    930                 935                 940

Phe Gln Asn Leu Asp Ser Ser Glu Ile Ser Leu Thr Asp Val Ser His
945                 950                 955                 960

Tyr Phe Asp Ser Asp Pro Thr Lys Leu Val Gln Gly Leu Arg Lys Asp
                965                 970                 975

Gly Arg Ala Pro Ser Ser Tyr Ile Ala Asp Thr Thr Ala Asn Ala
            980                 985                 990

Gln Val Arg Thr Leu Ser Glu Thr Val Arg Leu Asp Ala Arg Thr Lys
    995                 1000                1005

Leu Leu Asn Pro Lys Trp Tyr Glu Gly Met Met Lys Ser Gly Tyr Glu
    1010                1015                1020

Gly Val Arg Glu Ile Glu Lys Arg Leu Thr Asn Thr Val Gly Trp Ser
1025                1030                1035                1040

Ala Thr Ser Gly Gln Val Asp Asn Trp Val Tyr Glu Glu Ala Asn Ala
                1045                1050                1055

Thr Phe Ile Glu Asp Glu Ala Met Arg Lys Arg Leu Met Asp Thr Asn
            1060                1065                1070

Pro Asn Ser Phe Arg Lys Leu Val Gln Thr Phe Leu Glu Ala Ser Gly
        1075                1080                1085

Arg Gly Tyr Trp Glu Thr Ser Glu Glu Asn Leu Glu Lys Leu Arg Glu
    1090                1095                1100

Leu Tyr Ser Glu Val Glu Asp Lys Ile Glu Gly Ile Asp Arg
1105                1110                1115

<210> SEQ ID NO 37
<211> LENGTH: 511
<212> TYPE: DNA
<213> ORGANISM: Triticum aestivum
<220> FEATURE:
<221> NAME/KEY: unsure
<222> LOCATION: (317)
<221> NAME/KEY: unsure
<222> LOCATION: (332)
<221> NAME/KEY: unsure
<222> LOCATION: (382)
<221> NAME/KEY: unsure
```

<222> LOCATION: (403)
<221> NAME/KEY: unsure
<222> LOCATION: (413)
<221> NAME/KEY: unsure
<222> LOCATION: (415)
<221> NAME/KEY: unsure
<222> LOCATION: (419)
<221> NAME/KEY: unsure
<222> LOCATION: (471)
<221> NAME/KEY: unsure
<222> LOCATION: (490)

<400> SEQUENCE: 37

```
ttttttttta cattcacaac gaaccaccct ctttgttaaa ggtctgtatg gcatgttaca      60
acttttataa atcacaaatt atacaagttt cgactcagca aggcagaaga atatttcttc     120
ttggtcaaat gctggaactg gttgatcagt gaaatgagtt caccggtcaa ttccttcgat     180
cttgtcttca acctccgagt agagctccct gagcctttcc aagttatcct ctgatgtctc     240
ccaagtagcc cctgccattt gcttctagga aggttgaagc atttcctgaa cgaatggggg     300
tggtgtccat cagctcntcc tcatctcctc anccctcaatg aatgtggtat tgctcctcgt    360
aaaccagttg tccaactgcc cngatgttgc acccaaccaa cantattggc aancnttcnc     420
attcccctac tccctcaaag catcctcaac atccctcgta caactaggtc natactttgg     480
cccttgcacn aagagacgtc tccgaaagtc g                                    511
```

<210> SEQ ID NO 38
<211> LENGTH: 76
<212> TYPE: PRT
<213> ORGANISM: Triticum aestivum
<220> FEATURE:
<221> NAME/KEY: UNSURE
<222> LOCATION: (20)
<221> NAME/KEY: UNSURE
<222> LOCATION: (25)
<221> NAME/KEY: UNSURE
<222> LOCATION: (27)
<221> NAME/KEY: UNSURE
<222> LOCATION: (42)

<400> SEQUENCE: 38

```
Ala Thr Ser Gly Gln Leu Asp Asn Trp Phe Thr Arg Ser Asn Thr Thr
  1               5                  10                  15
Phe Ile Glu Xaa Glu Glu Met Arg Xaa Ser Xaa Trp Thr Pro Pro Pro
                 20                  25                  30
Phe Val Gln Glu Met Leu Gln Pro Ser Xaa Lys Gln Met Ala Gly Ala
             35                  40                  45
Thr Trp Glu Thr Ser Glu Asp Asn Leu Glu Arg Leu Arg Glu Leu Tyr
         50                  55                  60
Ser Glu Val Glu Asp Lys Ile Glu Gly Ile Asp Arg
 65                  70                  75
```

<210> SEQ ID NO 39
<211> LENGTH: 3257
<212> TYPE: DNA
<213> ORGANISM: Triticum aestivum

<400> SEQUENCE: 39

```
ccagggcgc caaggtcatc cccatcttcg ccggcgggct cgacttctcc ggccccatcg       60
agcgctacct cgtcgacccc atcaccaaga agccgttcgt gaacgccgtg gtgtcgctca     120
ccggggttcgc gctcgtcggc gggccggcca ggcaggacca ccccaaggcc atcgcctcgc    180
tgatgaagct agacgtgccg tacatcgtcg cgctgccgct cgtgttccag accacggagg    240
```

```
agtggctcaa cagcaccttg ggccttcacc ccatccaggt ggcgctgcag gttgcgctcc    300
cggagctcga cggcggcatg gagcccatcg tgttcgccgg ccgggacccg agatcaggga    360
agtcgcatgc attgcacaag agggtggagc agctctgcac tagagcgatc agatgggcag    420
aactcaagag gaaaactaag atggacaaga aactagccat caccgttttc agcttcccac    480
cagacaaggg caatgtcggc actgcagcat acctgaatgt cttcagttcc atctattctg    540
tcctcaagga tctcaagaag gatggctaca atgtcgaggg tcttccagag cacctgaag     600
aactcattga ggaggttatt catgataagg aggcccagtt caacagcccc aacctcaatg    660
ttgtttaccg catgaatgtg cgggagtacc aagcactcac ccctacgcc aacatgctgg     720
aggagaactg gggcaagcca cctgggcatc tcaactctga tggtgagaac ctccttgtct    780
atgggaagca gtatggcaac atcttcatcg gagtgcagcc cacttttggc tatgaaggtg    840
atccaatgcg gcttctgttc tcaaagtctg ccagccctca ccatgggttt gcggcatact    900
acactttgt tgagaagatc ttcaaggcag atgctgttct gcacttcggc acacacgggt     960
cccttgagtt catgcccggg aaacaagttg gaatgagtga tgcatgcttc cctgatagtc   1020
tgattggtaa catccccaac atctactact atgcagcaaa caaccccttca gaggcaacag   1080
tggccaagcg tcgaagctat gcaaacacca taagctacct gacaccacca gctgagaatg   1140
ccggtctgta caaggggctg aagcagctgt cagagctcat cgcctcttac cagtcactca   1200
aggacacggg ccgtggcaac cagattgtga gctcaatcat cagcactgca aaacagtgta   1260
acctggacaa ggatgttgac ttgcccgatg aaggcgagga gctcccagcc aatgagcgtg   1320
acctcgtcgt cgggaaggtg tatggaaagc tcatggagat agagtcacgg ctactgccat   1380
gtggtctgca tgtgataggt gagccaccaa ctgctgtcga agctgtggcc acattggtga   1440
acatagctgc ccttgaccgc ccagaggaga acatattctc gctgcccggc attcttgctg   1500
cgacggtggg caggaccatt gaagatgtgt acaggggtag cgacaagggc atactggctg   1560
atgttgaact cctgaagcag atcactgaag cttcacgagg tgccgtaggt gcctttgttg   1620
agaagactac aaacagcaaa ggcaagttg ttgatgttaa aagcaaactc agttccatcc    1680
ttggcttttgg tctctcagag ccatgggtgg agtacctgtc ccagaccaag ttcatcaggg   1740
cggacagaga taagctgagg accttgtttg gattcttggg agagtgcctg aagctgattg   1800
tggcagacaa tgagctggga gccttgaaga ctgcccttga gggaagctat gttgagcctg   1860
gccctggtgg tgatcccatc cgtaacccaa aggttctccc aacagggaag aacatccatg   1920
ctctcgaccc gcagtctatc ccgactgcag ctgccatgaa gagtgccaag attgttgtgg   1980
aacgtctgct ggagcggcaa aaggctgaca atggtggcaa gtatcctgag acaattgcac   2040
ttgtcttgtg gggcaccgac aacatcaaga cctacggcga gtcactggcc caggtgatgt   2100
ggatgcttgg tgtggagccg gttactgatg ggcttggccg tgtcaaccgt gtggagcccg   2160
tcagcattga ggagcttgga cgccctagga ttgatgtcgt cgtcaactgc tcgggtgtgt   2220
tcagagatct tttcatcaac cagatgaatc tgctggaccg ggcagtaaag atggttgctg   2280
aactggatga gccaattgag atgaactatg tgcgcaagca tgcccaggag caggcagagg   2340
agctcggtgt ctcggtaaga gaggcggcaa caaggatctt ctcaaatgca tcaggctctt   2400
actcgtcgaa tgtgaacttg gcagtggaga atgcatcatg gacagatgag aagcagctcc   2460
aggacatgta cctgagccgc aagtcttttg cgttcgacag tgatgctcca ggggtaggca   2520
tgctagagaa acgcaagacg tttgagcttg ctctagcaac agcagatgcc acattccaaa   2580
```

-continued

```
acctggactc gtcggagatc tcactgacgg atgtcagcca ctacttcgac tcagacccga    2640
cgaagctggt gcaagggctg cggaaggatg ggcgggcacc ttcatcgtac atagcagaca    2700
caaccacggc aaatgcacag gtgcggacat tgtcggagac ggtgcgtctt gatgcaagga    2760
caaagctact gaaccctagg tggtacgagg ggatgatgaa gagtggctat gagggagtta    2820
gagagatcga gaagcggctg acaaatactg ttggatggag tgcaacatcc gggcaggtgg    2880
acaactgggt ttacgaggaa gcaaatacca cattcattga agatgaagag atgaggaaga    2940
ggctgatgga caccaacccc aattcgttca ggaaactgct tcaaaccttc ctagaagcaa    3000
atggcagggg ctactgggag acatcagagg ataacttgga aaggctcagg gagctctact    3060
cggaggttga agacaagatc gaaggaattg accggtgaac tcatttcact gatcaaccag    3120
ttccagcatt tgaccaagaa gaaatattct tctgccttgc tgagtcgaaa cttgtataat    3180
ttgtgattta taaaagttgt aacatgccat acagacctttt aacaaagagg gtggttcgtt    3240
gtgaatgtaa aaaaaaa                                                  3257
```

<210> SEQ ID NO 40
<211> LENGTH: 1031
<212> TYPE: PRT
<213> ORGANISM: Triticum aestivum

<400> SEQUENCE: 40

```
Arg Gly Ala Lys Val Ile Pro Ile Phe Ala Gly Gly Leu Asp Phe Ser
  1               5                  10                  15

Gly Pro Ile Glu Arg Tyr Leu Val Asp Pro Ile Thr Lys Lys Pro Phe
             20                  25                  30

Val Asn Ala Val Val Ser Leu Thr Gly Phe Ala Leu Val Gly Gly Pro
         35                  40                  45

Ala Arg Gln Asp His Pro Lys Ala Ile Ala Ser Leu Met Lys Leu Asp
     50                  55                  60

Val Pro Tyr Ile Val Ala Leu Pro Leu Val Phe Gln Thr Thr Glu Glu
 65                  70                  75                  80

Trp Leu Asn Ser Thr Leu Gly Leu His Pro Ile Gln Val Ala Leu Gln
                 85                  90                  95

Val Ala Leu Pro Glu Leu Asp Gly Gly Met Glu Pro Ile Val Phe Ala
            100                 105                 110

Gly Arg Asp Pro Arg Ser Gly Lys Ser His Ala Leu His Lys Arg Val
        115                 120                 125

Glu Gln Leu Cys Thr Arg Ala Ile Arg Trp Ala Glu Leu Lys Arg Lys
    130                 135                 140

Thr Lys Met Asp Lys Lys Leu Ala Ile Thr Val Phe Ser Phe Pro Pro
145                 150                 155                 160

Asp Lys Gly Asn Val Gly Thr Ala Ala Tyr Leu Asn Val Phe Ser Ser
                165                 170                 175

Ile Tyr Ser Val Leu Lys Asp Leu Lys Lys Asp Gly Tyr Asn Val Glu
            180                 185                 190

Gly Leu Pro Glu Thr Pro Glu Leu Ile Glu Glu Val Ile His Asp
        195                 200                 205

Lys Glu Ala Gln Phe Asn Ser Pro Asn Leu Asn Val Val Tyr Arg Met
    210                 215                 220

Asn Val Arg Glu Tyr Gln Ala Leu Thr Pro Tyr Ala Asn Met Leu Glu
225                 230                 235                 240

Glu Asn Trp Gly Lys Pro Pro Gly His Leu Asn Ser Asp Gly Glu Asn
                245                 250                 255
```

-continued

```
Leu Leu Val Tyr Gly Lys Gln Tyr Gly Asn Ile Phe Ile Gly Val Gln
                260                 265                 270
Pro Thr Phe Gly Tyr Glu Gly Asp Pro Met Arg Leu Leu Phe Ser Lys
            275                 280                 285
Ser Ala Ser Pro His His Gly Phe Ala Ala Tyr Tyr Thr Phe Val Glu
            290                 295                 300
Lys Ile Phe Lys Ala Asp Ala Val Leu His Phe Gly Thr His Gly Ser
305                 310                 315                 320
Leu Glu Phe Met Pro Gly Lys Gln Val Gly Met Ser Asp Ala Cys Phe
                325                 330                 335
Pro Asp Ser Leu Ile Gly Asn Ile Pro Asn Ile Tyr Tyr Tyr Ala Ala
            340                 345                 350
Asn Asn Pro Ser Glu Ala Thr Val Ala Lys Arg Arg Ser Tyr Ala Asn
            355                 360                 365
Thr Ile Ser Tyr Leu Thr Pro Pro Ala Glu Asn Ala Gly Leu Tyr Lys
            370                 375                 380
Gly Leu Lys Gln Leu Ser Glu Leu Ile Ala Ser Tyr Gln Ser Leu Lys
385                 390                 395                 400
Asp Thr Gly Arg Gly Asn Gln Ile Val Ser Ser Ile Ile Ser Thr Ala
            405                 410                 415
Lys Gln Cys Asn Leu Asp Lys Asp Val Asp Leu Pro Asp Glu Gly Glu
            420                 425                 430
Glu Leu Pro Ala Asn Glu Arg Asp Leu Val Val Gly Lys Val Tyr Gly
            435                 440                 445
Lys Leu Met Glu Ile Glu Ser Arg Leu Leu Pro Cys Gly Leu His Val
            450                 455                 460
Ile Gly Glu Pro Pro Thr Ala Val Glu Ala Val Ala Thr Leu Val Asn
465                 470                 475                 480
Ile Ala Ala Leu Asp Arg Pro Glu Glu Asn Ile Phe Ser Leu Pro Gly
            485                 490                 495
Ile Leu Ala Ala Thr Val Gly Arg Thr Ile Glu Asp Val Tyr Arg Gly
            500                 505                 510
Ser Asp Lys Gly Ile Leu Ala Asp Val Glu Leu Leu Lys Gln Ile Thr
            515                 520                 525
Glu Ala Ser Arg Gly Ala Val Gly Ala Phe Val Glu Lys Thr Thr Asn
            530                 535                 540
Ser Lys Gly Gln Val Val Asp Val Lys Ser Lys Leu Ser Ser Ile Leu
545                 550                 555                 560
Gly Phe Gly Leu Ser Glu Pro Trp Val Glu Tyr Leu Ser Gln Thr Lys
                565                 570                 575
Phe Ile Arg Ala Asp Arg Asp Lys Leu Arg Thr Leu Phe Gly Phe Leu
            580                 585                 590
Gly Glu Cys Leu Lys Leu Ile Val Ala Asp Asn Glu Leu Gly Ala Leu
            595                 600                 605
Lys Thr Ala Leu Glu Gly Ser Tyr Val Glu Pro Gly Pro Gly Gly Asp
            610                 615                 620
Pro Ile Arg Asn Pro Lys Val Leu Pro Thr Gly Lys Asn Ile His Ala
625                 630                 635                 640
Leu Asp Pro Gln Ser Ile Pro Thr Ala Ala Met Lys Ser Ala Lys
            645                 650                 655
Ile Val Val Glu Arg Leu Leu Glu Arg Gln Lys Ala Asp Asn Gly Gly
            660                 665                 670
```

-continued

```
Lys Tyr Pro Glu Thr Ile Ala Leu Val Leu Trp Gly Thr Asp Asn Ile
            675                 680                 685

Lys Thr Tyr Gly Glu Ser Leu Ala Gln Val Met Trp Met Leu Gly Val
        690                 695                 700

Glu Pro Val Thr Asp Gly Leu Gly Arg Val Asn Arg Val Glu Pro Val
705                 710                 715                 720

Ser Ile Glu Glu Leu Gly Arg Pro Arg Ile Asp Val Val Asn Cys
                725                 730                 735

Ser Gly Val Phe Arg Asp Leu Phe Ile Asn Gln Met Asn Leu Leu Asp
                740                 745                 750

Arg Ala Val Lys Met Val Ala Glu Leu Asp Glu Pro Ile Glu Met Asn
            755                 760                 765

Tyr Val Arg Lys His Ala Gln Glu Gln Ala Glu Glu Leu Gly Val Ser
        770                 775                 780

Val Arg Glu Ala Ala Thr Arg Ile Phe Ser Asn Ala Ser Gly Ser Tyr
785                 790                 795                 800

Ser Ser Asn Val Asn Leu Ala Val Glu Asn Ala Ser Trp Thr Asp Glu
                805                 810                 815

Lys Gln Leu Gln Asp Met Tyr Leu Ser Arg Lys Ser Phe Ala Phe Asp
                820                 825                 830

Ser Asp Ala Pro Gly Val Gly Met Leu Glu Lys Arg Lys Thr Phe Glu
            835                 840                 845

Leu Ala Leu Ala Thr Ala Asp Ala Thr Phe Gln Asn Leu Asp Ser Ser
        850                 855                 860

Glu Ile Ser Leu Thr Asp Val Ser His Tyr Phe Asp Ser Asp Pro Thr
865                 870                 875                 880

Lys Leu Val Gln Gly Leu Arg Lys Asp Gly Arg Ala Pro Ser Ser Tyr
                885                 890                 895

Ile Ala Asp Thr Thr Thr Ala Asn Ala Gln Val Arg Thr Leu Ser Glu
            900                 905                 910

Thr Val Arg Leu Asp Ala Arg Thr Lys Leu Leu Asn Pro Arg Trp Tyr
        915                 920                 925

Glu Gly Met Met Lys Ser Gly Tyr Glu Gly Val Arg Glu Ile Glu Lys
930                 935                 940

Arg Leu Thr Asn Thr Val Gly Trp Ser Ala Thr Ser Gly Gln Val Asp
945                 950                 955                 960

Asn Trp Val Tyr Glu Glu Ala Asn Thr Thr Phe Ile Glu Asp Glu Glu
                965                 970                 975

Met Arg Lys Arg Leu Met Asp Thr Asn Pro Asn Ser Phe Arg Lys Leu
            980                 985                 990

Leu Gln Thr Phe Leu Glu Ala Asn Gly Arg Gly Tyr Trp Glu Thr Ser
        995                 1000                1005

Glu Asp Asn Leu Glu Arg Leu Arg Glu Leu Tyr Ser Glu Val Glu Asp
    1010                1015                1020

Lys Ile Glu Gly Ile Asp Arg
1025                1030

<210> SEQ ID NO 41
<211> LENGTH: 466
<212> TYPE: DNA
<213> ORGANISM: Zea mays
<220> FEATURE:
<221> NAME/KEY: unsure
<222> LOCATION: (14)
<221> NAME/KEY: unsure
<222> LOCATION: (21)
```

```
<221> NAME/KEY: unsure
<222> LOCATION: (212)
<221> NAME/KEY: unsure
<222> LOCATION: (373)
<221> NAME/KEY: unsure
<222> LOCATION: (376)
<221> NAME/KEY: unsure
<222> LOCATION: (393)
<221> NAME/KEY: unsure
<222> LOCATION: (414)
<221> NAME/KEY: unsure
<222> LOCATION: (416)
<221> NAME/KEY: unsure
<222> LOCATION: (441)
<221> NAME/KEY: unsure
<222> LOCATION: (452)
<221> NAME/KEY: unsure
<222> LOCATION: (456)
<221> NAME/KEY: unsure
<222> LOCATION: (463)

<400> SEQUENCE: 41
ctcctccccg tcanggcttc naccttctcc cccacttccg ccgcgagggc cctcctcccg     60
ggctccacct cccgcccact cttcctcgcc gcttcagctt cctcagggcg cattcaacca    120
tccaggaagg gactggactt ccgccgcggc cgattcaccg ttctgaaatt cgccgctccc    180
accgccgccg aacaggaggc gacggcgtcg gncgcgaagg agacccagcg ccccgtgtac    240
ccgttcgcgg ccatcgtggg gcaggacgag atgaagctct gcctgctgct caacgtcatc    300
gaccccaaga tcggcggcgt catgatcatg ggcgaacagg ggggaacggg gaaatccaac    360
aacggttcgg ctnccntccg tcgaacctgg ctncccgggt aatccgcctt cggncngtcg    420
ggggaacccc tttaaactcc ngaacccggg tngaancccg gangtg                   466

<210> SEQ ID NO 42
<211> LENGTH: 66
<212> TYPE: PRT
<213> ORGANISM: Zea mays
<220> FEATURE:
<221> NAME/KEY: UNSURE
<222> LOCATION: (23)

<400> SEQUENCE: 42

Arg Gly Arg Phe Thr Val Leu Lys Phe Ala Ala Pro Thr Ala Ala Glu
  1               5                  10                  15

Gln Glu Ala Thr Ala Ser Xaa Ala Lys Glu Thr Gln Arg Pro Val Tyr
             20                  25                  30

Pro Phe Ala Ala Ile Val Gly Gln Asp Glu Met Lys Leu Cys Leu Leu
         35                  40                  45

Leu Asn Val Ile Asp Pro Lys Ile Gly Gly Val Met Ile Met Gly Glu
     50                  55                  60

Gln Gly
 65

<210> SEQ ID NO 43
<211> LENGTH: 1377
<212> TYPE: DNA
<213> ORGANISM: Zea mays

<400> SEQUENCE: 43
ccacgcgtcc gctcctcccc gtcatggctt ccaccttctc ccccacttcc gccgcgaggg     60
ccctcctccc gggctccacc tcccgcccac tcttcctcgc cgcttcagct tcctcagggc    120
gcattcaacc atccaggaag ggactggact tccgccgcgg ccgattcacc gtctgcaatg    180
```

-continued

```
tcgccgctcc caccgccgcc gaacaggagg cgacggcgtc ggccgcgaag gagacccagc    240
gccccgtgta cccgttcgcg gccatcgtgg ggcaggacga gatgaagctc tgcctgctgc    300
tcaacgtcat cgaccccaag atcggcggcg tcatgatcat gggcgacagg ggcacgggga    360
agtccaccac cgtccgctcc ctcgtcgacc tgctcccgga catccgcgtc gtcgtcggcg    420
accccttcaa ctccgacccg gacgaccccg aggtcatggg cccgaggtc cgccaacggg     480 tcctgcaggg ggacaccggc ctccccgtca ccaccgccat agtcaccatg gtcgacctgc    540
ccctgggcgc caccgaggac cgcgtctgcg gcaccattga catcgagaag gcgctcaccg    600
agggcgtcaa ggcgttcgag cccggcctgc tcgccaaggc caacaggggc atactgtacg    660
tcgacgaggt caacctgctg gacgaccacc tcgtcgacgt gctgctggat ccgctgcgt     720 cggggtggaa cacggtggag agggagggta tctccatatc ccaccttgtt ggctttatct    780
taatgggttt tgttaacccg gaggaggggg agttcagccc ccagttgttg gaccggttcg    840
ggttgcaggc ccaggttgtt ccgttcaggg acccggagtt caggttgaaa atcttggagg    900
ggaggcttgt tttcgacagg aatccgaaga cgttccgtga gtcgtatcat gacgagcagg    960
agaagctcca gcagcagata tcatctgcac ggagtaacct tggcgctgtg cagattgacc   1020
atgacctccg tgtcaagata tccaaggtgt gctctgagtt gaacgttgat ggactcagag   1080
gtgacattgt gactaacagg gctgccaagg cgctggctgc gttgaaagga agggacagcg   1140
tcaccgtgga ggacattgct actgtcattc aaaactgctt gaggcatcgg ctccgcaagg   1200
atccgcttga atccattgac tcgggtttac ttgtcattga gaagttttat gaagtcttta   1260
gctagattgt tcttgaggta aatgttcctt tgtcacaatt tttggcggga accctcttgt   1320
tctgttactt tcataatgtt ctgctgttta ataatatctg gagcttgaat tggtatc      1377
```

<210> SEQ ID NO 44
<211> LENGTH: 413
<212> TYPE: PRT
<213> ORGANISM: Zea mays

<400> SEQUENCE: 44

```
Met Ala Ser Thr Phe Ser Pro Thr Ser Ala Ala Arg Ala Leu Leu Pro
  1               5                  10                  15

Gly Ser Thr Ser Arg Pro Leu Phe Leu Ala Ala Ser Ala Ser Ser Gly
             20                  25                  30

Arg Ile Gln Pro Ser Arg Lys Gly Leu Asp Phe Arg Arg Gly Arg Phe
         35                  40                  45

Thr Val Cys Asn Val Ala Ala Pro Thr Ala Ala Glu Gln Glu Ala Thr
     50                  55                  60

Ala Ser Ala Ala Lys Glu Thr Gln Arg Pro Val Tyr Pro Phe Ala Ala
 65                  70                  75                  80

Ile Val Gly Gln Asp Glu Met Lys Leu Cys Leu Leu Leu Asn Val Ile
                 85                  90                  95

Asp Pro Lys Ile Gly Gly Val Met Ile Met Gly Asp Arg Gly Thr Gly
            100                 105                 110

Lys Ser Thr Thr Val Arg Ser Leu Val Asp Leu Leu Pro Asp Ile Arg
        115                 120                 125

Val Val Val Gly Asp Pro Phe Asn Ser Asp Pro Asp Pro Glu Val
    130                 135                 140

Met Gly Pro Glu Val Arg Gln Arg Val Leu Gln Gly Asp Thr Gly Leu
145                 150                 155                 160

Pro Val Thr Thr Ala Ile Val Thr Met Val Asp Leu Pro Leu Gly Ala
```

```
                    165                 170                 175
Thr Glu Asp Arg Val Cys Gly Thr Ile Asp Ile Glu Lys Ala Leu Thr
                180                 185                 190
Glu Gly Val Lys Ala Phe Glu Pro Gly Leu Leu Ala Lys Ala Asn Arg
            195                 200                 205
Gly Ile Leu Tyr Val Asp Glu Val Asn Leu Leu Asp Asp His Leu Val
        210                 215                 220
Asp Val Leu Leu Asp Ser Ala Ala Ser Gly Trp Asn Thr Val Glu Arg
225                 230                 235                 240
Glu Gly Ile Ser Ile Ser His Leu Val Gly Phe Ile Leu Met Gly Phe
                245                 250                 255
Val Asn Pro Glu Glu Gly Glu Phe Ser Pro Gln Leu Leu Asp Arg Phe
                260                 265                 270
Gly Leu Gln Ala Gln Val Val Pro Phe Arg Asp Pro Glu Phe Arg Leu
            275                 280                 285
Lys Ile Leu Glu Gly Arg Leu Val Phe Asp Arg Asn Pro Lys Thr Phe
        290                 295                 300
Arg Glu Ser Tyr His Asp Glu Gln Glu Lys Leu Gln Gln Gln Ile Ser
305                 310                 315                 320
Ser Ala Arg Ser Asn Leu Gly Ala Val Gln Ile Asp His Asp Leu Arg
                325                 330                 335
Val Lys Ile Ser Lys Val Cys Ser Glu Leu Asn Val Asp Gly Leu Arg
                340                 345                 350
Gly Asp Ile Val Thr Asn Arg Ala Ala Lys Ala Leu Ala Ala Leu Lys
                355                 360                 365
Gly Arg Asp Ser Val Thr Val Glu Asp Ile Ala Thr Val Ile Pro Asn
            370                 375                 380
Cys Leu Arg His Arg Leu Arg Lys Asp Pro Leu Glu Ser Ile Asp Ser
385                 390                 395                 400
Gly Leu Leu Val Ile Glu Lys Phe Tyr Glu Val Phe Ser
                            405                 410

<210> SEQ ID NO 45
<211> LENGTH: 602
<212> TYPE: DNA
<213> ORGANISM: Oryza sativa
<220> FEATURE:
<221> NAME/KEY: unsure
<222> LOCATION: (345)
<221> NAME/KEY: unsure
<222> LOCATION: (462)
<221> NAME/KEY: unsure
<222> LOCATION: (490)
<221> NAME/KEY: unsure
<222> LOCATION: (497)
<221> NAME/KEY: unsure
<222> LOCATION: (507)
<221> NAME/KEY: unsure
<222> LOCATION: (509)
<221> NAME/KEY: unsure
<222> LOCATION: (517)
<221> NAME/KEY: unsure
<222> LOCATION: (539)
<221> NAME/KEY: unsure
<222> LOCATION: (543)
<221> NAME/KEY: unsure
<222> LOCATION: (545)
<221> NAME/KEY: unsure
<222> LOCATION: (555)
<221> NAME/KEY: unsure
<222> LOCATION: (557)
<221> NAME/KEY: unsure
<222> LOCATION: (559)
```

```
<221> NAME/KEY: unsure
<222> LOCATION: (574)

<400> SEQUENCE: 45
tacacacacc attgatattg agaaggcgct caccgatggt gtcaaggcgt tcgagcctgg      60
tttgcttgcc aaggccaaca gggggattct ttatgtggat gaggtcaatt tgttggatga    120
ccatctagta gatgtgcttc tggattctgc tgcgtcagga tggaacaccg tggagagaga    180
gggtatctcc atctcccacc ctgctcggtt catcctcatt gggtctgggt aaccccgagg    240 aagggagct ccggccacag ctgcttgacc ggtttggcat gcacgcgcag ttggtactgt      300
cagggatgct gaactcaagg gtgaaaatgt tgaagagaga ctccngtcga cagggattcc    360
aaagcttccg ttgatcctac tttggaggaa caagacaact ccaacagcaa attcaaccgc    420
tccgataacc ttggtgctgt gcaaattgac caatgatctt cntgttaaga ttccaaatgt    480
gtgcaaattn aatgttnatg gattaanang ggacatnttg actaacaagg ctgcaaagng    540
ttngnaacac caaangnang gacacttcac tgtnaaggac attgcactgt tttcccaact    600
gc                                                                   602

<210> SEQ ID NO 46
<211> LENGTH: 74
<212> TYPE: PRT
<213> ORGANISM: Oryza sativa

<400> SEQUENCE: 46

Thr Ile Asp Ile Glu Lys Ala Leu Thr Asp Gly Val Lys Ala Phe Glu
  1               5                  10                  15

Pro Gly Leu Leu Ala Lys Ala Asn Arg Gly Ile Leu Tyr Val Asp Glu
             20                  25                  30

Val Asn Leu Leu Asp Asp His Leu Val Asp Val Leu Leu Asp Ser Ala
         35                  40                  45

Ala Ser Gly Trp Asn Thr Val Glu Arg Glu Gly Ile Ser Ile Ser His
     50                  55                  60

Pro Ala Arg Phe Ile Leu Ile Gly Ser Gly
 65                  70

<210> SEQ ID NO 47
<211> LENGTH: 463
<212> TYPE: DNA
<213> ORGANISM: Oryza sativa
<220> FEATURE:
<221> NAME/KEY: unsure
<222> LOCATION: (200)
<221> NAME/KEY: unsure
<222> LOCATION: (298)
<221> NAME/KEY: unsure
<222> LOCATION: (304)
<221> NAME/KEY: unsure
<222> LOCATION: (348)
<221> NAME/KEY: unsure
<222> LOCATION: (380)
<221> NAME/KEY: unsure
<222> LOCATION: (389)
<221> NAME/KEY: unsure
<222> LOCATION: (392)
<221> NAME/KEY: unsure
<222> LOCATION: (433)
<221> NAME/KEY: unsure
<222> LOCATION: (438)
<221> NAME/KEY: unsure
<222> LOCATION: (452)
<221> NAME/KEY: unsure
<222> LOCATION: (455)
<221> NAME/KEY: unsure
```

```
<222> LOCATION: (457)

<400> SEQUENCE: 47
tgtatcctcc tcaccatggc ttccgccttc tcccccgcca ccgccgcgcc cgccgcgtcg      60
ccggccctct tctccgcctc cacctcccgg cctctctccc tcaccgccgc cgccgctgcc     120
gtctcagccc gtatcccgtc acggagaggg ttccgccgcg ccgcttcac cgtctgcaat      180 gtagccgccc cctccgccan ccagcaggag gctaaggcgg cgggcgcgaa ggagagccaa     240
cggccggtgt atccgttcgc ggcgatcgtg gggcaggacg agatgaagct gtgcctgntg     300
ctcnacgtca tcgaccctaa gatcggcggt gtcatgatca tgggagancg tgcaccggca     360
aatccaacaa cgtccgtcgn tcgtcgaant gntcccggat atcgcgtcgt tgttgggaac    420
ctttaaatcc gancctanga ttccgaggta tnggncntga ggc                       463

<210> SEQ ID NO 48
<211> LENGTH: 72
<212> TYPE: PRT
<213> ORGANISM: Oryza sativa
<220> FEATURE:
<221> NAME/KEY: UNSURE
<222> LOCATION: (15)
<221> NAME/KEY: UNSURE
<222> LOCATION: (48)
<221> NAME/KEY: UNSURE
<222> LOCATION: (50)
<221> NAME/KEY: UNSURE
<222> LOCATION: (64)

<400> SEQUENCE: 48

Arg Gly Arg Phe Thr Val Cys Asn Val Ala Ala Pro Ser Ala Xaa Gln
 1               5                  10                  15

Gln Glu Ala Lys Ala Ala Gly Ala Lys Glu Ser Gln Arg Pro Val Tyr
            20                  25                  30

Pro Phe Ala Ala Ile Val Gly Gln Asp Glu Met Lys Leu Cys Leu Xaa
        35                  40                  45

Leu Xaa Val Ile Asp Pro Lys Ile Gly Gly Val Met Ile Met Gly Xaa
    50                  55                  60

Arg Ala Pro Ala Asn Pro Thr Thr
65                  70

<210> SEQ ID NO 49
<211> LENGTH: 1408
<212> TYPE: DNA
<213> ORGANISM: Oryza sativa

<400> SEQUENCE: 49
gcacgagtgt atcctcctca ccatggcttc cgccttctcc ccgccaccg ccgcgcccgc       60 cgcgtcgccg ccctcttct ccgctccac ctcccgcct ctctccctca ccgccgccgc       120
cgctgccgtc tcagcccgta tccgtcacg gagagggttc gccgcggcc gcttcaccgt      180 ctgcaatgta gccgccccct ccgccaccca gcaggagct aaggcggcgg gcgcgaagga     240
gagccaacgg ccggtgtatc cgttcgcggc gatcgtgggg caggacgaga tgaagctgtg    300
cctgctgctc aacgtcatcg accctaagat cggcggtgtc atgatcatgg gagaccgtgg    360
caccggcaaa tccaccaccg tccgctcgct cgtcgacctg ctcccggata tccgcgtcgt    420
tgttggcgac ccttttcaatt ccgaccctga cgatcccgag gtcatgggcc tgaggtccg    480 ggaacgcgtg ctggaggggtg agaagcttcc tgttgtcacg gccaagatca ccatggtaga    540 tcttccccctt ggtgccactg aggatagagt ctgtggcacc attgatattg agaaggcgct   600
```

```
caccgatggt gtcaaggcgt tcgagcctgg tttgcttgcc aaggccaaca gggggattct      660
ttatgtggat gaggtcaatt tgttggatga ccatctagta gatgtgcttc tggattctgc      720
tgcgtcagga tggaacaccg tggagagaga gggtatctcc atctcccacc ctgctcggtt      780
catcctcatt gggtctggta accccgagga aggggagctc cggccacagc tgcttgaccg      840
gtttggcatg cacgcgcagg ttggtactgt cagggatgct gaactcaggg tgaaaattgt      900
tgaagagaga gctcggttcg acagggatcc aaaggcgttc cgtgagtcct acttggagga      960
acaagacaag ctccagcagc agatttcatc tgctcggagt aaccttggtg ctgtgcagat     1020
tgaccatgat cttcgtgtta agatttctaa agtgtgtgca gagttgaatg ttgatggatt     1080
aagaggggac attgtgacta acagggctgc caaggcgttg gcagcactca aaggcaggga     1140
cactgtcact gtagaggaca ttgccactgt tatccccaac tgcttgaggc atcggcttcg     1200
gaaggaccca cttgaatcaa ttgactcagg attgctcgtg gttgagaagt tttatgaagt     1260
cttcacctaa attattctgg aggtaaatgg ttttctatca gaaagttcgg caggagggct     1320
tttgtttgag tttaatgaca ttgtttcaga ggcttgaact tgatgtctat ttgtacatct     1380
atcattagta tagattttat tccccttc                                        1408
```

<210> SEQ ID NO 50
<211> LENGTH: 415
<212> TYPE: PRT
<213> ORGANISM: Oryza sativa

<400> SEQUENCE: 50

```
Met Ala Ser Ala Phe Ser Pro Ala Thr Ala Ala Pro Ala Ala Ser Pro
  1               5                  10                  15

Ala Leu Phe Ser Ala Ser Thr Ser Arg Pro Leu Ser Leu Thr Ala Ala
             20                  25                  30

Ala Ala Ala Val Ser Ala Arg Ile Pro Ser Arg Arg Gly Phe Arg Arg
         35                  40                  45

Gly Arg Phe Thr Val Cys Asn Val Ala Ala Pro Ser Ala Thr Gln Gln
     50                  55                  60

Glu Ala Lys Ala Ala Gly Ala Lys Glu Ser Gln Arg Pro Val Tyr Pro
 65                  70                  75                  80

Phe Ala Ala Ile Val Gly Gln Asp Glu Met Lys Leu Cys Leu Leu Leu
                 85                  90                  95

Asn Val Ile Asp Pro Lys Ile Gly Gly Val Met Ile Met Gly Asp Arg
            100                 105                 110

Gly Thr Gly Lys Ser Thr Thr Val Arg Ser Leu Val Asp Leu Leu Pro
        115                 120                 125

Asp Ile Arg Val Val Val Gly Asp Pro Phe Asn Ser Asp Pro Asp Asp
    130                 135                 140

Pro Glu Val Met Gly Pro Glu Val Arg Glu Arg Val Leu Glu Gly Glu
145                 150                 155                 160

Lys Leu Pro Val Val Thr Ala Lys Ile Thr Met Val Asp Leu Pro Leu
                165                 170                 175

Gly Ala Thr Glu Asp Arg Val Cys Gly Thr Ile Asp Ile Glu Lys Ala
            180                 185                 190

Leu Thr Asp Gly Val Lys Ala Phe Glu Pro Gly Leu Leu Ala Lys Ala
        195                 200                 205

Asn Arg Gly Ile Leu Tyr Val Asp Glu Val Asn Leu Leu Asp Asp His
    210                 215                 220
```

-continued

```
Leu Val Asp Val Leu Leu Asp Ser Ala Ala Ser Gly Trp Asn Thr Val
225                 230                 235                 240

Glu Arg Glu Gly Ile Ser Ile Ser His Pro Ala Arg Phe Ile Leu Ile
            245                 250                 255

Gly Ser Gly Asn Pro Glu Glu Gly Glu Leu Arg Pro Gln Leu Leu Asp
            260                 265                 270

Arg Phe Gly Met His Ala Gln Val Gly Thr Val Arg Asp Ala Glu Leu
            275                 280                 285

Arg Val Lys Ile Val Glu Glu Arg Ala Arg Phe Asp Arg Asp Pro Lys
290                 295                 300

Ala Phe Arg Glu Ser Tyr Leu Glu Glu Gln Asp Lys Leu Gln Gln Gln
305                 310                 315                 320

Ile Ser Ser Ala Arg Ser Asn Leu Gly Ala Val Gln Ile Asp His Asp
                325                 330                 335

Leu Arg Val Lys Ile Ser Lys Val Cys Ala Glu Leu Asn Val Asp Gly
                340                 345                 350

Leu Arg Gly Asp Ile Val Thr Asn Arg Ala Ala Lys Ala Leu Ala Ala
            355                 360                 365

Leu Lys Gly Arg Asp Thr Val Thr Val Glu Asp Ile Ala Thr Val Ile
370                 375                 380

Pro Asn Cys Leu Arg His Arg Leu Arg Lys Asp Pro Leu Glu Ser Ile
385                 390                 395                 400

Asp Ser Gly Leu Leu Val Val Glu Lys Phe Tyr Glu Val Phe Thr
                405                 410                 415

<210> SEQ ID NO 51
<211> LENGTH: 754
<212> TYPE: PRT
<213> ORGANISM: Pisum sativum

<400> SEQUENCE: 51

Met Gly Phe Ser Leu Thr His Thr Pro His Thr Thr Ala Ser Pro Asn
 1               5                  10                  15

Leu Gln Leu Arg Phe His Ser Leu Pro Pro Ser Phe Thr Ser Gln
            20                  25                  30

Pro Phe Leu Ser Leu His Ser Thr Phe Pro Pro Lys Arg Thr Val Pro
         35                  40                  45

Lys Leu Arg Ala Gln Ser Glu Asn Gly Ala Val Leu Gln Ala Ser Glu
     50                  55                  60

Glu Lys Leu Asp Ala Ser Asn Tyr Gly Arg Gln Tyr Phe Pro Leu Ala
 65                  70                  75                  80

Ala Val Ile Gly Gln Asp Ala Ile Lys Thr Ala Leu Leu Leu Gly Ala
                 85                  90                  95

Thr Asp Pro Arg Ile Gly Gly Ile Ala Ile Ser Gly Arg Arg Gly Thr
            100                 105                 110

Ala Lys Thr Ile Met Ala Arg Gly Met His Ala Ile Leu Pro Pro Ile
        115                 120                 125

Glu Val Val Gln Gly Ser Ile Ala Asn Ala Asp Pro Ser Cys Pro Glu
    130                 135                 140

Glu Trp Glu Asp Gly Leu Tyr Lys Arg Val Glu Tyr Asp Ser Asp Gly
145                 150                 155                 160

Asn Val Lys Thr His Ile Ile Lys Ser Pro Phe Val Gln Ile Pro Leu
                165                 170                 175

Gly Val Thr Glu Asp Arg Leu Ile Gly Ser Val Asp Val Glu Glu Ser
            180                 185                 190
```

-continued

```
Val Lys Thr Gly Thr Thr Val Phe Gln Pro Gly Leu Leu Ala Glu Ala
        195                 200                 205
His Arg Gly Val Leu Tyr Val Asp Glu Ile Asn Leu Leu Asp Glu Gly
        210                 215                 220
Ile Ser Asn Leu Leu Leu Asn Val Leu Thr Glu Gly Val Asn Ile Val
225                 230                 235                 240
Glu Arg Glu Gly Ile Ser Phe Arg His Pro Cys Arg Pro Leu Leu Ile
                245                 250                 255
Ala Thr Tyr Asn Pro Asp Glu Gly Ser Val Arg Glu His Leu Leu Asp
                260                 265                 270
Arg Ile Ala Ile Asn Leu Ser Ala Asp Leu Pro Met Ser Phe Glu Asn
        275                 280                 285
Arg Val Glu Ala Val Gly Ile Ala Thr Glu Phe Gln Asp Asn Cys Gly
        290                 295                 300
Gln Val Phe Lys Met Val Asp Glu Asp Thr Asp Asn Ala Lys Thr Gln
305                 310                 315                 320
Ile Ile Leu Ala Arg Glu Tyr Leu Lys Asp Val Thr Ile Ser Lys Glu
                325                 330                 335
Gln Leu Lys Tyr Leu Val Ile Glu Ala Leu Arg Gly Gly Val Gln Gly
                340                 345                 350
His Arg Ala Glu Leu Tyr Ala Ala Arg Val Ala Lys Cys Leu Ala Ala
        355                 360                 365
Leu Glu Gly Arg Glu Lys Val Tyr Val Asp Asp Leu Lys Lys Ala Val
        370                 375                 380
Glu Leu Val Ile Leu Pro Arg Ser Ile Ile Thr Asp Thr Pro Pro Glu
385                 390                 395                 400
Gln Gln Asn Gln Pro Pro Pro Pro Pro Pro Pro Gln Asn Gln Glu
                405                 410                 415
Ser Asn Glu Glu Gln Asn Glu Glu Glu Gln Glu Glu Glu Glu
                420                 425                 430
Asp Asp Asn Asp Glu Glu Asn Gly Gln Gln Gln Asp Gln Leu Pro Glu
        435                 440                 445
Glu Phe Ile Phe Asp Ala Glu Gly Gly Leu Val Asp Glu Lys Leu Leu
        450                 455                 460
Phe Phe Ala Gln Gln Ala Gln Arg Arg Arg Gly Lys Ala Gly Arg Ala
465                 470                 475                 480
Lys Asn Val Ile Phe Ser Glu Asp Arg Gly Arg Tyr Ile Lys Pro Met
                485                 490                 495
Leu Pro Lys Gly Pro Val Lys Arg Leu Ala Val Asp Ala Thr Leu Arg
                500                 505                 510
Ala Ala Ala Pro Tyr Gln Lys Leu Arg Arg Glu Lys Asp Thr Glu Asn
        515                 520                 525
Arg Arg Lys Val Tyr Val Glu Lys Thr Asp Met Arg Ala Lys Arg Met
        530                 535                 540
Ala Arg Lys Ala Gly Ala Leu Val Ile Phe Val Val Asp Ala Ser Gly
545                 550                 555                 560
Ser Met Ala Leu Asn Arg Met Gln Asn Ala Lys Gly Ala Ala Leu Lys
                565                 570                 575
Leu Leu Ala Glu Ser Tyr Thr Ser Arg Asp Gln Val Ser Ile Ile Pro
                580                 585                 590
Phe Arg Gly Asp Ser Ala Glu Val Leu Leu Pro Pro Ser Arg Ser Ile
                595                 600                 605
```

```
Ala Met Ala Arg Lys Arg Leu Glu Arg Leu Pro Cys Gly Gly Gly Ser
    610                 615                 620

Pro Leu Ala His Gly Leu Thr Thr Ala Val Arg Val Gly Leu Asn Ala
625                 630                 635                 640

Glu Lys Ser Gly Asp Val Gly Arg Ile Met Ile Val Ala Ile Thr Asp
                645                 650                 655

Gly Arg Ala Asn Ile Ser Leu Lys Arg Ser Asn Asp Pro Glu Ala Ala
            660                 665                 670

Ala Ala Ser Asp Ala Pro Lys Pro Thr Ser Gln Glu Leu Lys Asp Glu
        675                 680                 685

Ile Ile Glu Val Ala Ala Lys Ile Tyr Lys Thr Gly Met Ser Leu Leu
    690                 695                 700

Val Ile Asp Thr Glu Asn Lys Phe Val Ser Thr Gly Phe Ala Lys Glu
705                 710                 715                 720

Ile Ala Arg Val Ala Gln Gly Lys Tyr Tyr Tyr Leu Pro Asn Ala Ser
                725                 730                 735

Asp Ala Val Val Ser Leu Ala Thr Arg Glu Ala Leu Ala Ala Leu Lys
            740                 745                 750

Ser Ser

<210> SEQ ID NO 52
<211> LENGTH: 421
<212> TYPE: PRT
<213> ORGANISM: Glycine max

<400> SEQUENCE: 52

Met Ala Ser Ala Leu Gly Thr Ser Ser Ile Ala Val Leu Pro Ser Arg
1               5                   10                  15

Tyr Phe Ser Ser Ser Ser Lys Pro Ser Ile His Thr Leu Ser Leu
                20                  25                  30

Thr Ser Gly Gln Asn Tyr Gly Arg Lys Phe Tyr Gly Ile Gly Ile
            35                  40                  45

His Gly Ile Lys Gly Arg Ala Gln Leu Ser Val Thr Asn Val Ala Thr
        50                  55                  60

Glu Val Asn Ser Val Glu Gln Ala Gln Ser Ile Ala Ser Lys Glu Ser
65                  70                  75                  80

Gln Arg Pro Val Tyr Pro Phe Ser Ala Ile Val Gly Gln Asp Glu Met
                85                  90                  95

Lys Leu Cys Leu Leu Leu Asn Val Ile Asp Pro Lys Ile Gly Gly Val
                100                 105                 110

Met Ile Met Gly Asp Arg Gly Thr Gly Lys Ser Thr Thr Val Arg Ser
            115                 120                 125

Leu Val Asp Leu Leu Pro Glu Ile Lys Val Val Ala Gly Asp Pro Tyr
130                 135                 140

Asn Ser Asp Pro Gln Asp Pro Glu Phe Met Gly Val Glu Val Arg Glu
145                 150                 155                 160

Arg Val Leu Gln Gly Glu Glu Leu Ser Val Val Leu Thr Lys Ile Asn
                165                 170                 175

Met Val Asp Leu Pro Leu Gly Ala Thr Glu Asp Arg Val Cys Gly Thr
            180                 185                 190

Ile Asp Ile Glu Lys Ala Leu Thr Glu Gly Val Lys Ala Phe Glu Pro
        195                 200                 205

Gly Leu Leu Ala Lys Ala Asn Arg Gly Ile Leu Tyr Val Asp Glu Val
    210                 215                 220
```

-continued

```
Asn Leu Leu Asp Asp His Leu Val Asp Val Leu Leu Asp Ser Ala Ala
225                 230                 235                 240

Ser Gly Trp Asn Thr Val Glu Arg Glu Gly Ile Ser Ile Ser His Pro
                245                 250                 255

Ala Arg Phe Ile Leu Ile Gly Ser Gly Asn Pro Glu Glu Gly Glu Leu
            260                 265                 270

Arg Pro Gln Leu Leu Asp Arg Phe Gly Met His Ala Gln Val Gly Thr
        275                 280                 285

Val Arg Asp Ala Glu Leu Arg Val Lys Ile Val Glu Glu Arg Gly Arg
    290                 295                 300

Phe Asp Lys Asn Pro Lys Glu Phe Arg Asp Ser Tyr Lys Ala Glu Gln
305                 310                 315                 320

Glu Lys Leu Gln Gln Gln Ile Thr Ser Ala Arg Ser Val Leu Ser Ser
                325                 330                 335

Val Gln Ile Asp Gln Asp Leu Lys Val Lys Ile Ser Lys Val Cys Ala
            340                 345                 350

Glu Leu Asn Val Asp Gly Leu Arg Gly Asp Ile Val Thr Asn Arg Ala
        355                 360                 365

Ala Lys Ala Leu Ala Ala Leu Lys Gly Arg Asp Asn Val Ser Ala Glu
    370                 375                 380

Asp Ile Ala Thr Val Ile Pro Asn Cys Leu Arg His Arg Leu Arg Lys
385                 390                 395                 400

Asp Pro Leu Glu Ser Ile Asp Ser Gly Leu Leu Val Thr Glu Lys Phe
                405                 410                 415

Tyr Glu Val Phe Ser
                420

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 53
ggaagcatag catgcaaacc ac                                              22

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 54
cacttcaatg ggtggaagca tag                                             23
```

MAGNESIUM CHELATASE

This application claims priority benefit of U.S. Provisional Application No. 60/137,461 filed Jun. 4, 1999.

FIELD OF THE INVENTION

This invention is in the field of plant molecular biology. More specifically, this invention pertains to nucleic acid fragments encoding magnesium chelatase subunit in plants and seeds.

BACKGROUND OF THE INVENTION

Magnesium chelatase catalyzes the insertion of the magnesium cation ($Mg^{2+}$) into protoporphyrin IX, the branch-point in the tetrapyrrole biosynthetic pathways leading to (bacterio)chlorophyll synthesis. In photosynthetic bacteria, magnesium chelatase activity requires three different subunits encoded by the genes bchD, bchH and bchI (Willows, R. D. and Beale, S. I., (1998) *J. Biol. Chem.* 273:34206–34213). It has been proposed that the BchH subunit initially forms a complex with protoporphyrin IX while the Bch I and BchD subunits form a complex in an ATP-dependent activation step. The BchI-BchD complex then inserts the magnesium cation into the BchH-bound protoporphyrin IX in an ATP-dependent reaction (Willows, R. D. and Beale, S. I. supra).

Similarly in higher plants, three distinct proteins, CHLD, CHLH, and CHLI, encoded by the genes ChlD, ChlH and ChlI respectively (Papenbrock J. et al., (1997) *Plant J.* 12:981–990) are required for magnesium chelatase activity. They share significant sequence similarity with their bacterial counterparts, further suggesting that the mechanism of magnesium chelation proceeds more or less similarly in plants and bacteria (Guo, R. et al., (1998) *Plant Physiol.* 116:605–615).

Since magnesium chelatase is an enzyme specific for chlorophyll synthesis, it presents a potential target for discovery and development of herbicides nontoxic to man and animals. Isolation of more genes encoding magnesium chelatase subunits provides a wider array of possible targets, thereby increasing the chances of successfully identifying promising herbicide candidates.

SUMMARY OF THE INVENTION

The present invention concerns an isolated polynucleotide comprising a nucleotide sequence selected from the group consisting of: (a) a first nucleotide sequence encoding a polypeptide of at least 50 amino acids having at least 80% identity based on the Clustal method of alignment when compared to a polypeptide selected from the group consisting of SEQ ID NOs:14, 38, 42, and 48; (b) a second nucleotide sequence encoding a polypeptide of at least 100 amino acids having at least 80% identity based on the Clustal method of alignment when compared to a polypeptide selected from the group consisting of SEQ ID NOs:6, 10, and 30; (c) a third nucleotide sequence encoding a polypeptide of at least 100 amino acids having at least 85% identity based on the Clustal method of alignment when compared to a polypeptide of SEQ ID NO:26; (d) a fourth nucleotide sequence encoding a polypeptide of at least 100 amino acids having at least 90% identity based on the Clustal method of alignment when compared to a polypeptide selected from the group consisting of SEQ ID NOs:2, 20, and 34; (e) a fifth nucleotide sequence encoding a polypeptide of at least 100 amino acids having at least 95% identity based on the Clustal method of alignment when compared to a polypeptide of SEQ ID NO:24; (f) a sixth nucleotide sequence encoding a polypeptide of at least 130 amino acids having at least 85% identity based on the Clustal method of alignment when compared to a polypeptide of SEQ ID NO:28; (g) a seventh nucleotide sequence encoding a polypeptide of at least 150 amino acids having at least 80% identity based on the Clustal method of alignment when compared to a polypeptide of SEQ ID NO:32; (h) an eighth nucleotide sequence encoding a polypeptide of at least 250 amino acids having at least 85% identity based on the Clustal method of alignment when compared to a polypeptide of SEQ ID NO:44; (i) a ninth nucleotide sequence encoding a polypeptide of at least 250 amino acids having at least 90% identity based on the Clustal method of alignment when compared to a polypeptide of SEQ ID NO:22; 0) a tenth nucleotide sequence encoding a polypeptide of at least 380 amino acids having at least 90% identity based on the Clustal method of alignment when compared to a polypeptide of SEQ ID NO:8; (k) an eleventh nucleotide sequence encoding a polypeptide of at least 400 amino acids having at least 85% identity based on the Clustal method of alignment when compared to a polypeptide of SEQ ID NO:50; (1) a twelfth nucleotide sequence encoding a polypeptide of at least 400 amino acids having at least 90% identity based on the Clustal method of alignment when compared to a polypeptide of SEQ ID NO:4; (m) a thirteenth nucleotide sequence encoding a polypeptide of at least 750 amino acids having at least 90% identity based on the Clustal method of alignment when compared to a polypeptide of SEQ ID NO:12; (n) a fourteenth nucleotide sequence encoding a polypeptide of at least 1110 amino acids having at least 95% identity based on the Clustal method of alignment when compared to a polypeptide of SEQ ID NO:36; and (o) a fifteenth nucleotide sequence comprising the complement of (a), (b), (c), (d), (e), (f), (g), (h), (i), (0), (k), (1), (m), or (n).

In a second embodiment, it is preferred that the isolated polynucleotide of the claimed invention comprises a nucleotide sequence which comprises a nucleic acid sequence selected from the group consisting of SEQ ID NOs:1, 3, 5, 7, 9, 11, 13, 19, 21, 23, 25, 27, 29, 31, 33, 35, 37, 41, 43, 47, and 49 that codes for the polypeptide selected from the group consisting of SEQ ID NOs:2, 4, 6, 8, 10, 12, 14, 20, 22, 24, 26, 28, 30, 32, 34, 36, 38, 42,44, 48, and 50.

In a third embodiment, this invention concerns an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 19, 21, 23, 25, 27, 29, 31, 33, 35, 37, 41, 43, 47, and 49 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns a host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing a host cell comprising a chimeric gene of the present invention or an isolated polynucleotide of the present invention, the process comprising either transforming or transfecting a compatible host cell with a chimeric gene or isolated polynucleotide of the present invention.

In a seventh embodiment, the invention concerns a magnesium chelatase subunit polypeptide selected from the group consisting of: (a) a polypeptide of at least 50 amino acids having at least 80% identity based on the Clustal method of alignment when compared to a polypeptide selected from the group consisting of SEQ ID NOs:14, 38, 42, and 48; (b) a polypeptide of at least 100 amino acids having at least 80% identity based on the Clustal method of alignment when compared to a polypeptide selected from the group consisting of SEQ ID NOs:6, 10, and 30; (c) a polypeptide of at least 100 amino acids having at least 85% identity based on the Clustal method of alignment when compared to a polypeptide of SEQ ID NO:26; (d) a polypeptide of at least 100 amino acids having at least 90% identity based on the Clustal method of alignment when compared to a polypeptide selected from the group consisting of SEQ ID NOs:2, 20, and 34; (e) a polypeptide of at least 100 amino acids having at least 95% identity based on the Clustal method of alignment when compared to a polypeptide of SEQ ID NO:24; (f) a polypeptide of at least 130 amino acids having at least 85% identity based on the Clustal method of alignment when compared to a polypeptide of SEQ ID NO:28; (g) a polypeptide of at least 150 amino acids having at least 80% identity based on the Clustal method of alignment when compared to a polypeptide of SEQ ID NO:32; (h) a polypeptide of at least 250 amino acids having at least 85% identity based on the Clustal method of alignment when compared to a polypeptide of SEQ ID NO:44; (i) a polypeptide of at least 250 amino acids having at least 90% identity based on the Clustal method of alignment when compared to a polypeptide of SEQ ID NO:22; (j) a polypeptide of at least 380 amino acids having at least 90% identity based on the Clustal method of alignment when compared to a polypeptide of SEQ ID NO:8; (k) a polypeptide of at least 400 amino acids having at least 85% identity based on the Clustal method of alignment when compared to a polypeptide of SEQ ID NO:50; (l) a polypeptide of at least 400 amino acids having at least 90% identity based on the Clustal method of alignment when compared to a polypeptide of SEQ ID NO:4; (m) a polypeptide of at least 750 amino acids having at least 90% identity based on the Clustal method of alignment when compared to a polypeptide of SEQ ID NO:12; and (n) a polypeptide of at least 1110 amino acids having at least 95% identity based on the Clustal method of alignment when compared to a polypeptide of SEQ ID NO:36.

In an eighth embodiment, the invention relates to a method of selecting an isolated polynucleotide that affects the level of expression of a magnesium chelatase subunit polypeptide or enzyme activity in a host cell, preferably a plant cell, the method comprising the steps of: (a) constructing an isolated polynucleotide of the present invention or a chimeric gene of the present invention; (b) introducing the isolated polynucleotide or the chimeric gene into a host cell; (c) measuring the level of the magnesium chelatase subunit polypeptide or enzyme activity in the host cell containing the isolated polynucleotide; and (d) comparing the level of the magnesium chelatase subunit polypeptide or enzyme activity in the host cell containing the isolated polynucleotide with the level of the magnesium chelatase subunit polypeptide or enzyme activity in the host cell that does not contain the isolated polynucleotide.

In a ninth embodiment, the invention concerns a method of obtaining a nucleic acid fragment encoding a substantial portion of a magnesium chelatase subunit polypeptide, preferably a plant magnesium chelatase subunit polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 19, 21, 23, 25, 27, 29, 31, 33, 35, 37, 41, 43, 47, and 49 and the complement of such nucleotide sequences; and amplifying a nucleic acid fragment (preferably a cDNA inserted in a cloning vector) using the oligonucleotide primer. The amplified nucleic acid fragment preferably will encode a substantial portion of a magnesium chelatase subunit amino acid sequence.

In a tenth embodiment, this invention relates to a method of obtaining a nucleic acid fragment encoding all or a substantial portion of the amino acid sequence encoding a magnesium chelatase subunit polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide or an isolated polypeptide of the present invention.

In a twelfth embodiment, this invention concerns a method for positive selection of a transformed cell comprising: (a) transforming a host cell with the chimeric gene of the present invention or a construct of the present invention; and (b) growing the transformed host cell, preferably a plant cell, such as a monocot or a dicot, under conditions which allow expression of the magnesium chelatase subunit polynucleotide in an amount sufficient to complement a null mutant to provide a positive selection means.

In a thirteenth embodiment, this invention relates to a method of altering the level of expression of a magnesium chelatase subunit in a host cell comprising: (a) transforming a host cell with a chimeric gene of the present invention; and (b) growing the transformed host cell under conditions that are suitable for expression of the chimeric gene wherein expression of the chimeric gene results in production of altered levels of the magnesium chelatase subunit in the transformed host cell.

A further embodiment of the instant invention is a method for evaluating at least one compound for its ability to inhibit the activity of a magnesium chelatase subunit, the method comprising the steps of: (a) transforming a host cell with a chimeric gene comprising a nucleic acid fragment encoding a magnesium chelatase subunit polypeptide, operably linked to at least one suitable regulatory sequence; (b) growing the transformed host cell under conditions that are suitable for expression of the chimeric gene wherein expression of the chimeric gene results in production of the encoded magnesium chelatase subunit in the transformed host cell; (c) optionally purifying the magnesium chelatase subunit polypeptide expressed by the transformed host cell; (d) treating the magnesium chelatase subunit polypeptide with a compound to be tested; and (e) comparing the activity of the magnesium chelatase subunit polypeptide that has been treated with a test compound to the activity of an untreated magnesium chelatase subunit polypeptide, thereby selecting compounds with potential for inhibitory activity.

Another embodiment of the instant invention is a method for evaluating at least one compound for its ability to inhibit the activity of a magnesium chelatase subunit, the method comprising the steps of: (a) transforming a host cell or plant with a chimeric gene comprising a nucleic acid fragment encoding a magnesium chelatase subunit polypeptide, operably linked to at least one suitable regulatory sequence; (b) growing the transformed host cell or plant under conditions that are suitable for expression of the chimeric gene wherein expression of the chimeric gene results in production of the magnesium chelatase subunit encoded by the operably linked nucleic acid fragment in the transformed host cell or plant; (c) treating the transformed host cell or plant with a compound to be tested; and (d) comparing the viability of the transformed host cell or plant that has been treated with a test compound to the viability of an untreated transformed host cell or plant, thereby selecting compounds with potential for inhibitory activity. Methods for determining viability of cells and plants are well-known to those of ordinary skill in the art.

A further embodiment of the instant invention is a method for conferring, to a host cell or plant, resistance to herbicidal compounds acting on magnesium chelatase, the method comprising the steps of: (a) transforming a host cell or plant with a chimeric gene comprising a nucleic acid fragment encoding a magnesium chelatase subunit polypeptide, operably linked to at least one suitable regulatory sequence; and (b) growing the transformed host cell or plant under conditions that are suitable for expression of the chimeric gene wherein expression of the chimeric gene results in production of the magnesium chelatase subunit encoded by the operably linked nucleic acid fragment in the transformed host cell or plant, and results further in resistance of the transformed host cell or plant to herbicidal compounds acting on magnesium chelatase.

BRIEF DESCRIPTION OF THE DRAWINGS AND SEQUENCE LISTINGS

The invention can be more fully understood from the following detailed description, the accompanying, drawings and the Sequence Listing which form a part of this application.

FIGS. 1A, 1B and 1C depict the amino acid sequence alignment of the CHLD proteins encoded by the nucleotide sequences derived from a contig assembled from corn clone p0005.cbmff04r and PCR product (SEQ ID NO:4), and soybean clone sdp4c.pk022.h18 (SEQ ID NO:12), and the CHLD protein from *Pisum sativum* (NCBI GI No. 3913218; SEQ ID NO:51). Amino acids which are conserved among all and at least two sequences with an amino acid at that position are indicated with an asterisk (*). Dashes are used by the program to maximize alignment of the sequences.

FIGS. 2A and 2B depict the amino acid sequence alignment of CHLI proteins encoded by the nucleotide sequences derived from corn clone csc1c.pk004.p11 (SEQ ID NO:44) and rice clone rls48.pk0001.h1 (SEQ ID NO:50), and the CHLI protein from *Glycine max* (NCBI GI No. 3334150; SEQ ID NO:52). Amino acids which are conserved among all and at least two sequences with an amino acid at that position are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide SEQ ID NOs:1, 5, 9, 13, 15, 19, 23, 33, 37, 41, 45, and 47 correspond to nucleotide SEQ ID NOs:1, 3, 5, 7, 9, 11, 13, 15, 17, 19, 23, and 21, respectively, presented in U.S. Provisional Application No. 60/137,461, filed Jun. 4, 1999. Amino acid SEQ ID NOs:2, 6, 10, 14, 16, 20, 24, 34, 38, 42, 46, and 48 correspond to amino acid SEQ ID NOs:2, 4, 6, 8, 10, 12, 14, 16, 18, 20, 24, and 22, respectively, presented in U.S. Provisional Application No. 60/137,461, filed Jun. 4, 1999. The sequence descriptions and Sequence Listing attached hereto comply with the rules governing nucleotide and/or amino acid sequence disclosures in patent applications as set forth in 37 C.F.R. §1.821–1.825.

TABLE 1

Magnesium Chelatase Subunits

| Protein (Plant Source) | Clone Destination | Status | SEQ ID NO: (Nucleotide) | (Amino Acid) |
|---|---|---|---|---|
| CHLD (Corn) | p0005.cbmff04r | EST | 1 | 2 |
| CHLD (Corn) | Contig of: p0005.cbmff04r (FIS) PCR product | CGS | 3 | 4 |
| CHLD (Rice) | rsl1n.pk001.j9 | EST | 5 | 6 |
| CHLD (Rice) | rsl1n.pk001.j9 | FIS | 7 | 8 |
| CHLD (Soybean) | sdp4c.pk022.h18 | EST | 9 | 10 |
| CHLD (Soybean) | sdp4c.pk022.h18 (FIS) | CGS | 11 | 12 |
| CHLD (Soybean) | ses4d.pk0043.c6 | EST | 13 | 14 |
| CHLD (Wheat) | wr1.pk0064.e2 | EST | 15 | 16 |
| CHLD (Wheat) | wr1.pk0064.e2 | FIS | 17 | 18 |
| CHLH (Corn) | cdt1c.pk001.o1 | EST | 19 | 20 |
| CHLH (Corn) | cdt1c.pk001.o1 | FIS | 21 | 22 |
| CHLH (Corn) | chp2.pk0007.d5 | EST | 23 | 24 |
| CHLH (Corn) | chp2.pk0014.h1 | EST | 25 | 26 |
| CHLH (Corn) | p0019.clwaa84r | EST | 27 | 28 |
| CHLH (Corn) | p0088.clrih26r | EST | 29 | 30 |
| CHLH (Corn) | p0110.cgsmo74r | EST | 31 | 32 |
| CHLH (Rice) | rlr2.pk0018.e9 | EST | 33 | 34 |
| CHLH (Rice) | rlr2.pk0018.e9 | FIS | 35 | 36 |
| CHLH (Wheat) | wdk4c.pk005.f24 | EST | 37 | 38 |
| CHLH (Wheat) | wdk4c.pk005.f24 | FIS | 39 | 40 |
| CHLI (Corn) | csc1c.pk004.p11 | EST | 41 | 42 |
| CHLI (Corn) | csc1c.pk004.p11 (FIS) | CGS | 43 | 44 |
| CHLI (Rice) | rlr72.pk0014.f9 | EST | 45 | 46 |
| CHLI (Rice) | rls48.pk0001.h1 | EST | 47 | 48 |
| CHLI (Rice) | rls48.pk0001.h1 (FIS) | CGS | 49 | 50 |

SEQ ID NOs:53 and 54 are oligonucleotide primers used in PCR amplification of 5' end of the cDNA represented in clone p0005.cbmff04r.

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 19, 21, 23, 25, 27, 29, 31, 33, 35, 37, 41, 43, 47, and 49, or the complement of such sequences.

The term "isolated polynucleotide" refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example.antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 19, 21, 23, 25, 27, 29, 31, 33, 35, 37, 41, 43, 47, and 49 and the complement of such nucleotide sequences may be used in methods of selecting an isolated polynucleotide that affects the expression of a magnesium chelatase subunit polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or a chimeric gene of the present invention; introducing the isolated polynucleotide or the chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 or 130 amino acids, more preferably at least 150 amino acids, still more preferably at least 200 amino acids, and most preferably at least 250, 380, 400, 750 or 1110 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' Non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. "Expression" may also refer to the translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refer to the production of gene product(s) in transgenic organisms in amounts or proportions that differ from that of normal or non-transformed organisms.

"Null mutant" refers to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence encoding a polypeptide of at least 50 amino acids having at least 80% identity based on the Clustal method of alignment when compared to a polypeptide selected from the group consisting of SEQ ID NOs:14, 38, 42, and 48; (b) a second nucleotide sequence encoding a polypeptide of at least 100 amino acids having at least 80% identity based on the Clustal method of alignment when compared to a polypeptide selected from the group consisting of SEQ ID NOs:6, 10, and 30; (c) a third nucleotide sequence encoding a polypeptide of at least 100 amino acids having at least 85% identity based on the Clustal method of alignment when compared to a polypeptide of SEQ ID NO:26; (d) a fourth nucleotide sequence encoding a polypeptide of at least 100 amino acids having at least 90% identity based on the Clustal method of alignment when compared to a polypep- tide selected from the group consisting of SEQ ID NOs:2, 20, and 34; (e) a fifth nucleotide sequence encoding a polypeptide of at least 100 amino acids having at least 95% identity based on the Clustal method of alignment when compared to a polypeptide of SEQ ID NO:24; (f) a sixth nucleotide sequence encoding a polypeptide of at least 130 amino acids having at least 85% identity based on the Clustal method of alignment when compared to a polypeptide of SEQ ID NO:28; (g) a seventh nucleotide sequence encoding a polypeptide of at least 150 amino acids having at least 80% identity based on the Clustal method of alignment when compared to a polypeptide of SEQ ID NO:32; (h) an eighth nucleotide sequence encoding a polypeptide of at least 250 amino acids having at least 85% identity based on the Clustal method of alignment when compared to a polypeptide of SEQ ID NO:44; (i) a ninth nucleotide sequence encoding a polypeptide of at least 250 amino acids having at least 90% identity based on the Clustal method of alignment when compared to a polypeptide of SEQ ID NO:22; 0) a tenth nucleotide sequence encoding a polypeptide of at least 380 amino acids having at least 90% identity based on the Clustal method of alignment when compared to a polypeptide of SEQ ID NO:8; (k) an eleventh nucleotide sequence encoding a polypeptide of at least 400 amino acids having at least 85% identity based on the Clustal method of alignment when compared to a polypeptide of SEQ ID NO:50; (1) a twelfth nucleotide sequence encoding a polypeptide of at least 400 amino acids having at least 90% identity based on the Clustal method of alignment when compared to a polypeptide of SEQ ID NO:4; (m) a thirteenth nucleotide sequence encoding a polypeptide of at least 750 amino acids having at least 90% identity based on the Clustal method of alignment when compared to a polypeptide of SEQ ID NO:12; (n) a fourteenth nucleotide sequence encoding a polypeptide of at least 11 10 amino acids having at least 95% identity based on the Clustal method of alignment when compared to a polypeptide of SEQ ID NO:36; and (o) a fifteenth nucleotide sequence comprising the complement of (a), (b), (c), (d), (e), (f), (g), (h), (i), (0), (k), (1), (m), or (n).

Preferably, the nucleotide sequence comprises a nucleic acid sequence selected from the group consisting of SEQ ID NOs:1, 3, 5, 7, 9, 11, 13, 19, 21, 23, 25, 27, 29, 31, 33, 35, 37, 41, 43, 47, and 49, that codes for the polypeptide selected from the group consisting of SEQ ID NOs:2, 4, 6, 8, 10, 12, 14, 20, 22, 24, 26, 28, 30, 32, 34, 36, 38, 42, 44, 48, and 50.

Nucleic acid fragments encoding at least a substantial portion of several magnesium chelatase subunits have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other magnesium chelatase subunits, either as cDNAs or genomic DNAs, could be isolated directly by using all or a substantial portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 19, 21, 23, 25, 27, 29, 31, 33, 35, 37, 41, 43, 47, and 49 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a magnesium chelatase subunit polypeptide, preferably a substantial portion of a plant magnesium chelatase subunit polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3,5,7,9, 11, 13, 19,21,23,25,27,29,31, 33,35, 37,41,43,47, and 49, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a magnesium chelatase subunit polypeptide.

Availability of the instant nucleotide and deduced amino acid sequences facilitates immunological screening of cDNA expression libraries. Synthetic peptides representing substantial portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of magnesium cation ($Mg^{2+}$) insertion into protoporphyrin IX in those cells, consequently leading to changes in the level of chlorophyll pigmentation in those cells. Another effect would be changes in the level of resistance of those cells to herbicidal compounds acting on magnesium chelatase; overexpression of magnesium chelatase subunits may confer resistance to herbicidal compounds acting on magnesium chelatase. The nucleic acid fragments of the instant invention may also be used for overexpression in bacterial or yeast hosts, thereby efficiently producing large amounts of the encoded polypeptides which could then be used for screening different compounds for potential herbicidal activity. Host cells (e.g., plant, cyanobacteria) overexpressing magnesium chelatase may also be used directly for screening different compounds for potential herbicidal activity by exposing said host cell directly to the compound being tested.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the chimeric gene described above may be further supplemented by directing the coding sequence to encode the instant polypeptides with appropriate intracellular targeting sequences such as transit sequences (Keegstra (1989) Cell 56:247–253), signal sequences or sequences encoding endoplasmic reticulum localization (Chrispeels (1991) Ann. Rev. Plant Phys. Plant Mol. Biol. 42:21–53), or nuclear localization signals (Raikhel (1992) Plant Phys. 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a magnesium chelatase subunit polypeptide selected from the group consisting of: (a) a polypeptide of at least 50 amino acids having at least 80% identity based on the Clustal method of alignment when compared to a polypeptide selected from the group consisting of SEQ ID NOs:14, 38, 42, and 48; (b) a polypeptide of at least 100 amino acids having at least 80% identity based on the Clustal method of alignment when compared to a polypeptide selected from the group consisting of SEQ ID NOs:6, 10, and 30; (c) a polypeptide of at least 100 amino acids having at least 85% identity based on the Clustal method of alignment when compared to a polypeptide of SEQ ID NO:26; (d) a polypeptide of at least 100 amino acids having at least 90% identity based on the Clustal method of alignment when compared to a polypeptide selected from the group consisting of SEQ ID NOs:2, 20, and 34; (e) a polypeptide of at least 100 amino acids having at least 95% identity based on the Clustal method of alignment when compared to a polypeptide of SEQ ID NO:24; (f) a polypeptide of at least 130 amino acids having at least 85% identity based on the Clustal method of alignment when compared to a polypeptide of SEQ ID NO:28; (g) a polypeptide of at least 150 amino acids having at least 80% identity based on the Clustal method of alignment when compared to a polypeptide of SEQ ID NO:32; (h) a polypeptide of at least 250 amino acids having at least 85% identity based on the Clustal method of alignment when compared to a polypeptide of SEQ ID NO:44; (i) a polypeptide of at least 250 amino acids having at least 90% identity based on the Clustal method of alignment when compared to a polypeptide of SEQ ID NO:22; 0) a polypeptide of at least 380 amino acids having at least 90% identity based on the Clustal method of alignment when compared to a polypeptide of SEQ ID NO:8; (k) a polypeptide of at least 400 amino acids having at least 85% identity based on the Clustal method of alignment when compared to a polypeptide of SEQ ID NO:50; (1) a polypeptide of at least 400 amino acids having at least 90% identity based on the Clustal method of alignment when compared to a polypeptide of SEQ ID NO:4; (m) a polypeptide of at least 750 amino acids having at least 90% identity based on the Clustal method of alignment when compared to a polypeptide of SEQ ID NO:12; and (n) a polypeptide of at least I 110 amino acids having at least 95% identity based on the Clustal method of alignment when compared to a polypeptide of SEQ ID NO:36.

The instant polypeptides (or substantial portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded magnesium chelatase subunit. An example of a vector for high level expression of the instant polypeptides in a bacterial host is provided (Example 8).

Additionally, the instant polypeptides can be used as a target to facilitate design and/or identification of inhibitors of those enzymes that may be useful as herbicides. This is desirable because the polypeptides described herein catalyze various steps in magnesium chelation of protoporphyrin IX, en route to chlorophyll production. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) Genomics 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) Am. J Hum. Genet. 32:314–331).

The production and use of plant gene-derived probes for use in genetic mapping is described in Bernatzky and Tanksley (1986) Plant Mol. Biol. Reporter 4:37–4 1. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: Nonmammalian Genomic Analysis: A Practical Guide, Academic press 1996, pp. 319–346, and references cited therein).

In another embodiment, nucleic acid probes derived from the instant nucleic acid sequences may be used in direct fluorescence in situ hybridization (FISH) mapping (Trask (1991) Trends Genet. 7:149–154). Although current methods of FISH mapping favor use of large clones (several to several hundred KB; see Laan et al. (1995) Genome Res. 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) J Lab. Clin. Med. 11:95–96), polymorphism of PCR-amplified fragments (CAPS; Sheffield et al. (1993) Genomics 16:325–332), allele-specific ligation (Landegren et al. (1988) Science 241:1077–1080), nucleotide extension reactions (Sokolov (1990) Nucleic acid Res. 18:3671), Radiation Hybrid Mapping (Walter et al. (1997) Nat. Genet. 7:22–28) and Happy Mapping (Dear and Cook (1989) Nucleic Acid Res. 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) Proc. Natl. Acad. Sci USA 86:9402–9406; Koes et al. (1995) Proc. Natl. Acad. Sci USA 92:8149–8153; Bensen et al. (1995) Plant Cell 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn, rice, soybean and wheat tissues were prepared. The characteristics of the libraries are described below. Corn developmental stages are explained in the publication "How a corn plant develops" from the Iowa State University Coop. Ext. Service Special Report No. 48 reprinted June 1993.

TABLE 2 cDNA Libraries from Corn, Rice, Soybean, and Wheat

| Library | Tissue | Clone |
|---|---|---|
| cdt1c | Corn Developing Tassel | cdt1c.pk001.o1 |
| chp2 | Corn (B73 and MK593) 11 Day Old Leaf Treated 24 Hours With Herbicides* | chp2.pk0007.d5<br>chp2.pk0014.h1 |
| csc1c | Corn 20-Day-Old Seedling (Germination Cold Stress) | csc1c.pk004.p11 |
| p0005 | Corn Immature Ear | p0005.cbmff04r |
| p0019 | Corn Green Leaves (V5-7) After Mechanical Wounding for 1 Hour | p0019.clwaa84r |
| p0088 | Corn Leaf: Induced Resistance; Harvested Prior To Spontaneous Lesion Formation; About One Month After Planting In Green House**;*** | p0088.clrih26r |
| p0110 | Corn (Stages V3/V4) Leaf Tissue Minus Midrib Harvested 4 Hours, 24 Hours and 7 Days After Infiltration With Salicylic Acid, Pooled** | p0110.cgsmo74r |
| r1r2 | Resistant Rice Leaf 15 Days After Germination, 2 Hours After Infection of Strain Magaporthe grisea 4360-R-62 (AVR2-YAMO) | r1r2.pk0018.e9 |
| r1r72 | Resistant Rice Leaf 15 Days After Germination, 72 Hours After Infection of Strain Magaporthe grisea 4360-R-62 (AVR2-YAMO) | r1r72.pk0014.f9 |
| r1s48 | Susceptible Rice Leaf 15 Days After Germination, 48 Hours After Infection of Strain Magaporthe grisea 4360-R-67 (AVR2-YAMO) | r1s48.pk0001.h1 |
| rsl1n | Rice 15-Day-Old Seedling** | rsl1n.pk001.j9 |
| sdp4c | Soybean Developing Pod (10–12 mm) | sdp4c.pk022.h18 |
| ses4d | Soybean Embryogenic Suspension 4 Days After Subculture | ses4d.pk0043.c6 |
| wdk4c | Wheat Developing Kernel, 21 Days After Anthesis | wdk4c.pk005.f24 |
| wr1 | Wheat Root From 7-Day-Old Seedling Light Grown | wr1.pk0064.e2 |

*Application of 2-[(2,4-dihydro-2,6,9-trimethyl[1]benzothiopyrano[4,3-c]pyrazol-8-yl)carbonyl]-1,3-cyclohexanedione S,S-dioxide (synthesis and methods of using this compound are described in WO 97/19087, incorporated herein by reference) and 2-[(2,3-dihydro-5,8-dimethylspiro[4H-1-benzothiopyran-4,2'-[1,3]dioxolan]-6-yl)carbonyl]-1,3-cyclohexanedione S,S-dioxide (also named 2-[(2,3-dihydro-5,8-dimethylspiro[4H-1-benzothiopyran-4,2'-[1, 3]dioxolan]-6-yl)carbonyl]-3-hydroxy-2-cyclohexen-1-one S,S-dioxide; synthesis and methods of using this compound are described in WO 97/01550, incorporated herein by reference)
**These libraries were normalized essentially as described in U.S. Pat. No. 5,482,845, incorporated herein by reference.
***This particular corn line is described in Simmons et al. (1998) MPMI 11:1110–1118.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding magnesium chelatase subunit were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Magnesium Chelatase Subunit CHLD

The BLASTX search using the EST sequences from clones rsl1n.pk001.j9, sdp4c.pk022.h18, ses4d.pk0043.c6 and wr1.pk0064.e2 revealed similarity of the proteins encoded by the cDNAs to magnesium chelatase subunit CHLD from *Pisum sativum* (NCBI GenBank Identifier No. 3913218). The BLAST results for each of these ESTs are shown in Table 3:

TABLE 3

BLAST Results for Clones Encoding Polypeptides Homologous to Magnesium Chelatase Subunit CHLD

| Clone | BLAST pLog Score (3913218) |
|---|---|
| rsl1n.pk001.j9 | 68.70 |
| sdp4c.pk022.h18 | 36.40 |
| ses4d.pk0043.c6 | 21.52 |
| wr1.pk0064.e2 | 61.00 |

The BLASTX search using the EST sequences from clone p0005.cbmff04r revealed similarity of the protein encoded by the cDNA to magnesium chelatase subunit CHLD from *Nicotiana tabacum* (NCBI GenBank Identifier No. 3913240) with a pLog score of 58.70.

The sequence of a substantial portion of the cDNA insert from clone p0005.cbmff04r is shown in SEQ ID NO:1; the deduced amino acid sequence of this substantial portion of the cDNA is shown in SEQ ID NO:2. The sequence of a substantial portion of the cDNA insert from clone rsl1n.pk001.j9 is shown in SEQ ID NO:5; the deduced amino acid sequence of this substantial portion of the cDNA is shown in SEQ ID NO:6. The sequence of a substantial portion of the cDNA insert from clone sdp4c.pk022.h18 is shown in SEQ ID NO:9; the deduced amino acid sequence of this substantial portion of the cDNA is shown in SEQ ID NO:10. The sequence of a substantial portion of the cDNA insert from clone ses4d.pk0043.c6 is shown in SEQ ID NO:13; the deduced amino acid sequence of this cDNA is shown in SEQ ID NO:14. The sequence of a substantial portion of the cDNA insert from clone wrl.pk0064.e2 is shown in SEQ ID NO:15; the deduced amino acid sequence of this cDNA is shown in SEQ ID NO:16. BLAST scores and probabilities indicate that the instant nucleic acid fragments encode substantial portions of magnesium chelatase subunit CHLD.

The BLASTX search using the EST sequences from clones listed in Table 4 revealed similarity of the polypeptides encoded by the cDNAs to magnesium chelatase subunit CHLD from *Hordeum vulgare* (NCBI GenBank Identifier (GI) No. 6066383), *Nicotiana tabacum* (NCBI GI No. 3913240), and *Pisum sativum* (NCBI GI No. 3913218). Shown in Table 4 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 4

BLAST Results for Sequences Encoding Polypeptides Homologous to Magnesium Chelatase Subunit CHLD

| Clone | Status | BLAST Results NCBI GI No. | pLog Score |
|---|---|---|---|
| Contig of: p0005.cbmff04r (FIS) PCR product | CGS | 3913240 | >254.00 |
| rsl1n.pk001.j9 | FIS | 6066383 | >254.00 |
| sdp4c.pk022.h18 (FIS) | CGS | 3913218 | >254.00 |
| wrl.pk0064.e2 | FIS | 6066383 | 103.00 |

In generating the PCR product whose sequence was used in a contig with the sequence of the entire insert in clone p0005.cbmff04r to generate the nucleotide sequence encoding the entire protein, the following oligonucleotides were used as primers:

Cgs252-RIa: 5' GGAAGCATAGCATGCAAACCAC 3' SEQ ID NO:53

Cgs252-ROa: 5° CACTTCAATGGGTGGAAGCATAG 3' SEQ ID NO:54

Template DNA used in separate reactions was DNA from a cDNA library made from cDNA derived from corn developing kernel (embryo and endosperm) 10 days after pollination (library cbn10); DNA from a cDNA library made from cDNA derived from the root of 7-day-old corn seedling (library crl); and DNA from a cDNA library made from cDNA derived from a corn embryo 20 days after pollination (library cho1c). The PCR reaction mix contained the following components, with GC polymerase mix, GC buffer, and GC melt obtained from Clonetech:

| | |
|---|---|
| GC Polymerase Mix, 50X | 1 μL |
| GC Buffer, 5X | 10 μL |
| GC Melt, 1M | 10 μL |
| dNTPs, 2 mM each | 5 μL |
| Template DNA | 1–5 μL |
| Primer 1, 10 μM (SEQ ID NO: 53) | 1 μL |
| Primer 2, 10 μM (SEQ ID NO: 54) | 1 μL |
| Water to a total volume of | 50 μL |

PCR conditions were as follows:
1 cycle of 94° C., 1 minute;
10 cycles of 94° C., 30 seconds,
 68° C., 30 seconds,
 72° C., 4 minutes,
with annealing temperature decreasing 0.5° C. per cycle to a final temperature of 63° C.;
25 cycles of 94° C., 30 seconds,
 63° C., 30 seconds,
 72° C., 4 minutes;
1 cycle of 72° C., 7 minutes;
Hold at 15° C. until next step.

PCR products were subcloned using Topo TA Cloning kit (Invitrogen) and sequenced. Sequencing of PCR products yielded nucleotides 1–395 in SEQ ID NO:4 which overlaps with the sequence of the entire insert in clone p0005.cbmff04r. A contig was thus assembled, shown in SEQ ID NO:4.

FIGS. 1A–1C present an alignment of the amino acid sequences set forth in SEQ ID NOs:4 and 12 and the *Pisum sativum* sequence (NCBI GI No. 3913218; SEQ ID NO:51). The data in Table 5 represents a calculation of the percent identity of the amino acid sequences set forth in SEQ ID NOs:4 and 12 and the *Pisum sativum* sequence (NCBI GI No. 3913218; SEQ ID NO:51).

TABLE 5

Percent Identity of Amino Acid Sequences Deduced From the Nucleotide Sequences of cDNA Clones Encoding Polypeptides Homologous to Magnesium Chelatase Subunit CHLD

| SEQ ID NO. | Percent Identity to NCBI GI No. 3913218; SEQ ID NO: 51 |
|---|---|
| 4 | 78.0 |
| 12 | 85.1 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode all or a substantial portion of a magnesium chelatase subunit CHLD.

Example 4

Characterization of cDNA Clones Encoding Magnesium Chelatase Subunit CHLH

The BLASTX search using the EST sequences from clones cdt1c.pk001.o1 and chp2.pk0007.d5 revealed similarity of the proteins encoded by the cDNAs to magnesium chelatase subunit CHLH from *Glycine max* (NCBI GenBank Identifier (GI) No. 3059095) with pLog scores of 50.22 and 90.30, respectively. The BLASTX search using the EST sequences from clones rlr2.pk0018.e9 and wdk4c.pk005.f24 revealed similarity of the proteins encoded by the cDNAs to magnesium chelatase subunit CHLH from *Hordeum vulgare* (NCBI GI No. 2130042) with pLog scores of 60.70 and 13.05, respectively.

The sequence of a substantial portion of the cDNA insert from clone cdt1c.pk001.o1 is shown in SEQ ID NO:19; the deduced amino acid sequence of this substantial portion of the cDNA is shown in SEQ ID NO:20. The sequence of a substantial portion of the cDNA insert from clone chp2.pk0007.d5 is shown in SEQ ID NO:23; the deduced amino acid sequence of this substantial portion of the cDNA is shown in SEQ ID NO:24. The sequence of a substantial portion of the cDNA insert from clone rlr2.pk0018.e9 is shown in SEQ ID NO:33; the deduced amino acid sequence of this substantial portion of the cDNA is shown in SEQ ID NO:34. The sequence of a substantial portion of the cDNA insert from clone wdk4c.pk005.f24 is shown in SEQ ID NO:37; the deduced amino acid sequence of this substantial portion of the cDNA is shown in SEQ ID NO:38. BLAST scores and probabilities indicate that the instant nucleic acid fragments encode substantial portions of magnesium chelatase subunit CHLH.

The BLASTX search using the EST sequences from clones listed in Table 6 revealed similarity of the polypeptides encoded by the cDNAs to magnesium chelatase subunit CHLH from *Glycine max* (NCBI GI No. 7450927) and *Hordeum vulgare* (NCBI GI No. 2130042). Shown in Table 6 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 6

BLAST Results for Sequences Encoding Polypeptides
Homologous to Magnesium Chelatase Subunit CHLH

| | | BLAST Results | |
|---|---|---|---|
| Clone | Status | NCBI GI No. | pLog Score |
| cdt1c.pk001.o1 | FIS | 7450927 | 125.00 |
| chp2.pk0014.h1 | EST | 2130042 | 37.40 |
| p0019.clwaa84r | EST | 2130042 | 52.30 |
| p0088.clrih26r | EST | 2130042 | 40.15 |
| p0110.cgsmo74r | EST | 2130042 | 49.70 |
| rlr2.pk0018.e9 | FIS | 2130042 | >254.00 |
| wdk4c.pk005.f24 | FIS | 2130042 | >254.00 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode a substantial portion of a magnesium chelatase subunit CHLH.

Example 5

Characterization of cDNA Clones Encoding Majnesiurn Chelatase Subunit CHLI

The BLASTX search using the EST sequences from clones csc1c.pk004.p11, rls48.pk0001.h1 and rlr72.pk0014.f9 revealed similarity of the proteins encoded by the cDNAs to magnesium chelatase subunit CHLI from *Glycine max* (NCBI GI No. 3334150) with pLog scores of 20.70, 21.52 and 57.00, respectively.

The sequence of a substantial portion of the cDNA insert from clone csc1c.pk004.p11 is shown in SEQ ID NO:41; the deduced amino acid sequence of this substantial portion of the cDNA is shown in SEQ ID NO:42. The sequence of a substantial portion of the cDNA insert from clone rls48.pk0001.h1 is shown in SEQ ID NO:47; the deduced amino acid sequence of this substantial portion of the cDNA is shown in SEQ ID NO:48. The sequence of a substantial portion of the cDNA insert from clone rlr72.pk0014.f9 is shown in SEQ ID NO:45; the deduced amino acid sequence of this substantial portion of the cDNA is shown in SEQ ID NO:46. BLAST scores and probabilities indicate that the instant nucleic acid fragments encode substantial portions of magnesium chelatase subunit CHLI.

The BLASTX search using the EST sequences from clones listed in Table 7 revealed similarity of the polypeptides encoded by the cDNAs to magnesium chelatase subunit CHLI from *Glycine max* (NCBI GI No. 3334150). Shown in Table 7 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 7

BLAST Results for Sequences Encoding Polypeptides
Homologous to Magnesium Chelatase Subunit CHLI

| Clone | Status | BLAST pLog Score NCBI GI No. 3334150 |
|---|---|---|
| csc1c.pk004.p11 (FIS) | CGS | 164.00 |
| rls48.pk0001.h1 (FIS) | CGS | 180.00 |

FIGS. 2A–2B present an alignment of the amino acid sequences set forth in SEQ ID NOs:44 and 50 and the *Glycine max* sequence (NCBI GI No. 3334150; SEQ ID NO:52). The data in Table 8 represents a calculation of the percent identity of the amino acid sequences set forth in SEQ ID NOs:44 and 50 and the *Glycine max* sequence (NCBI GI No. 3334150; SEQ ID NO:52).

TABLE 8

Percent Identity of Amino Acid Sequences Deduced From the
Nucleotide Sequences of cDNA Clones Encoding Polypeptides
Homologous to Magnesium Chelatase Subunit CHLI

| SEQ ID NO. | Percent Identity to NCBI GI No. 3334150; SEQ ID NO: 52 |
|---|---|
| 44 | 72.6 |
| 50 | 78.1 |

Sequence alignments and percent identity calculations were performed using the Megalign program of the LASERGENE bioinf6rmatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode all or a substantial portion of a magnesium chelatase subunit CHLI.

Example 6

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110–2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL 1-Blue (Epicurian Coli XL-1 Blue™; Stratagene). Bacterial transformants can be screened by restriction enzyme digestion of plasmid DNA and limited nucleotide sequence analysis using the dideoxy chain termination method (SequenaseTm DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of mercury (Hg). The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 7

Expression of Chimeric Genes in Dicot Cells

A seed-specific construct composed of the promoter and transcription terminator from the gene encoding the P subunit of the seed storage protein phaseolin from the bean *Phaseolus vulgaris* (Doyle et al. (1986) *J Biol. Chem.* 261:9228–9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed construct.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS0001/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed construct comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches of mercury (Hg). The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 9

Evaluating Compounds for Their Ability to Inhibit the Activity of Magnesium Chelatase The polypeptides described herein may be produced using any number of methods known to those skilled in the art. Such methods include, but are not limited to, expression in bacteria as described in Example 8, or expression in eukaryotic cell culture, inplanta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzymes. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, anmmonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for magnesium chelatase subunits CHLD, CHLH and CHLI are presented by Papenbrock, J. et al. (1997), *Plant J* 12:981–990 and Guo, R. et al. (1998), *Plant Physiol.* 116:605–615.

What is claimed is:

1. An isolated polynucleotide comprising:
   (a) a nucleotide sequence encoding a polypeptide having magnesium chelatase subunit CHLD activity, wherein the amino acid sequence of the polypeptide and the amino acid sequence of SEQ ID NO:4 have at least 90% sequence identity based on the Clustal alignment method with multiple alignment default parameters of Gap Penalty=10, Gap Length Penalty=10, and pairwise alignment default parameters of Ktuple=1, Gap Penalty=3, Window=5 and Diagonals Saved=5, or
   (b) the complement of the nucleotide sequence, wherein the complement and the nucleotide sequence contain the same number of nucleotides and are 100% complementary.

2. The polynucleotide of claim 1, wherein the amino acid sequence of the polypeptide and the amino acid sequence of SEQ ID NO:4 have at least 95% sequence identity based on the Clustal alignment method.

3. The polynucleotide of claim 1, wherein the nucleotide sequence comprises the nucleotide sequence of SEQ ID NO:3.

4. The polynucleotide of claim wherein 1, the polypeptide comprises the amino acid sequence of SEQ ID NO:4.

5. A vector comprising the polynucleotide of any one of claims 1–4 inclusive.

6. A recombinant,DNA construct comprising the polynucleotide of any one of claims 1–4 inclusive operably linked to a regulatory sequence.

7. A method for transforming a cell comprising transforming a cell with the polynucleotide of any one of claims 1–4 inclusive.

8. A cell comprising the recombinant DNA construct of claim 6.

9. A method for producing a plant comprising transforming plant cell with the polynucleotide of any one of claims 1–4 inclusive and regenerating a plant from the transformed plant cell.

10. A plant comprising the recombinant DNA construct of claim 6.

11. A seed comprising the recombinant DNA construct of claim 6.

* * * * *

UNITED STATES PATENT AND TRADEMARK OFFICE
CERTIFICATE OF CORRECTION

PATENT NO. : 6,570,063 B1  
APPLICATION NO. : 09/585173  
DATED : May 27, 2003  
INVENTOR(S) : Butler et al.

Page 1 of 1

It is certified that error appears in the above-identified patent and that said Letters Patent is hereby corrected as shown below:

Claims section, column 115, line 1, claim 4: delete "of claim wherein 1," and insert therefor --of claim 1, wherein--.

Column 115, line 5, claim 6: after "recombinant" delete ",".

Column 116, line 2, claim 9: insert --a-- before "plant cell".

Bottom of columns 31 and 32, Sequence Listing section: please delete entire section beginning at bottom of columns 31 and 32 through bottom of columns 113 and 114 and replace with Amended Sequence Listing filed on February 6, 2003 and entered March 28, 2003.

Signed and Sealed this

Fifth Day of September, 2006

JON W. DUDAS  
*Director of the United States Patent and Trademark Office*